US012078796B2

(12) United States Patent
Ito et al.

(10) Patent No.: US 12,078,796 B2
(45) Date of Patent: Sep. 3, 2024

(54) ENDOSCOPE LIGHT SOURCE DEVICE, ENDOSCOPE APPARATUS, OPERATING METHOD OF ENDOSCOPE LIGHT SOURCE DEVICE, AND LIGHT AMOUNT ADJUSTING METHOD

(71) Applicant: OLYMPUS CORPORATION, Tokyo (JP)

(72) Inventors: Takeshi Ito, Hino (JP); Satoshi Tanaka, Hachioji (JP); Koichiro Ito, Akiruno (JP)

(73) Assignee: OLYMPUS CORPORATION, Tokyo (JP)

( * ) Notice: Subject to any disclaimer, the term of this patent is extended or adjusted under 35 U.S.C. 154(b) by 610 days.

(21) Appl. No.: 17/315,439

(22) Filed: May 10, 2021

(65) Prior Publication Data
US 2021/0278658 A1 Sep. 9, 2021

Related U.S. Application Data

(63) Continuation of application No. PCT/JP2018/041802, filed on Nov. 12, 2018.

(51) Int. Cl.
*G02B 23/24* (2006.01)
*A61B 1/00* (2006.01)
(Continued)

(52) U.S. Cl.
CPC ...... *G02B 23/2469* (2013.01); *A61B 1/00057* (2013.01); *A61B 1/0655* (2022.02); *G02B 23/2484* (2013.01); *G02B 26/007* (2013.01)

(58) Field of Classification Search
CPC ............ G02B 23/2469; G02B 23/2484; G02B 26/007; G02B 23/2423; G02B 27/141;
(Continued)

(56) References Cited

U.S. PATENT DOCUMENTS 10,512,512 B2 * 12/2019 Richmond ............. A61B 90/30
2016/0223807 A1 8/2016 Otani
(Continued)

FOREIGN PATENT DOCUMENTS

JP 1988-271217 A 11/1988
JP 2016-144624 A 8/2016
(Continued)

OTHER PUBLICATIONS

WO 2016/129162, Murakita, Aug. 18, 2016, English Translation (Year: 2016).*
(Continued)

*Primary Examiner* — Peggy A Neils
(74) *Attorney, Agent, or Firm* — Scully, Scott, Murphy & Presser, P.C.

(57) ABSTRACT

An endoscope light source device includes a light source device and a light source controller. A first light and a second light are narrow band light in a blue region. A third light is in a green region. A fourth light is in a red region. A first light amount ratio is a ratio of a sum of the light amounts of the first light and the second light, the light amount of the third light, and the light amount of the fourth light. A second light amount ratio is a light amount ratio of the first light and the second light. The light source controller adjusts the light amount ratio of the first light and the second light to achieve the second light amount ratio so as to adjust the color representation from a yellow region to a red region in an image of an object.

19 Claims, 11 Drawing Sheets

(51) Int. Cl.
*A61B 1/06* (2006.01)
*G02B 26/00* (2006.01)

(58) Field of Classification Search
CPC .............. A61B 1/00057; A61B 1/0655; A61B 1/00006; A61B 1/0638; A61B 1/07; H04N 23/555; H04N 23/56; H04N 23/76; H04N 25/134; F21V 33/0068; F21Y 2113/10; F21Y 2115/10
See application file for complete search history.

(56) References Cited

U.S. PATENT DOCUMENTS

| | | |
|---|---|---|
| 2016/0306163 A1 | 10/2016 | Sakai et al. |
| 2017/0319053 A1 | 11/2017 | Kamee et al. |
| 2018/0027165 A1 | 1/2018 | Murakita |
| 2018/0084980 A1 | 3/2018 | Watanabe et al. |
| 2018/0228355 A1 | 8/2018 | Daidoji et al. |

FOREIGN PATENT DOCUMENTS

| | | |
|---|---|---|
| WO | 2015/159676 A1 | 10/2015 |
| WO | 2016/120907 A1 | 8/2016 |
| WO | 2016/129162 A1 | 8/2016 |
| WO | 2016/194150 A1 | 12/2016 |
| WO | 2017/061003 A1 | 4/2017 |

OTHER PUBLICATIONS

WO 2015/159676, Sakai et al , Oct. 22, 2015, English Translation (Year: 2015).*
International Search Report dated Jan. 22, 2019 issued in PCT/JP2018/041802.

* cited by examiner

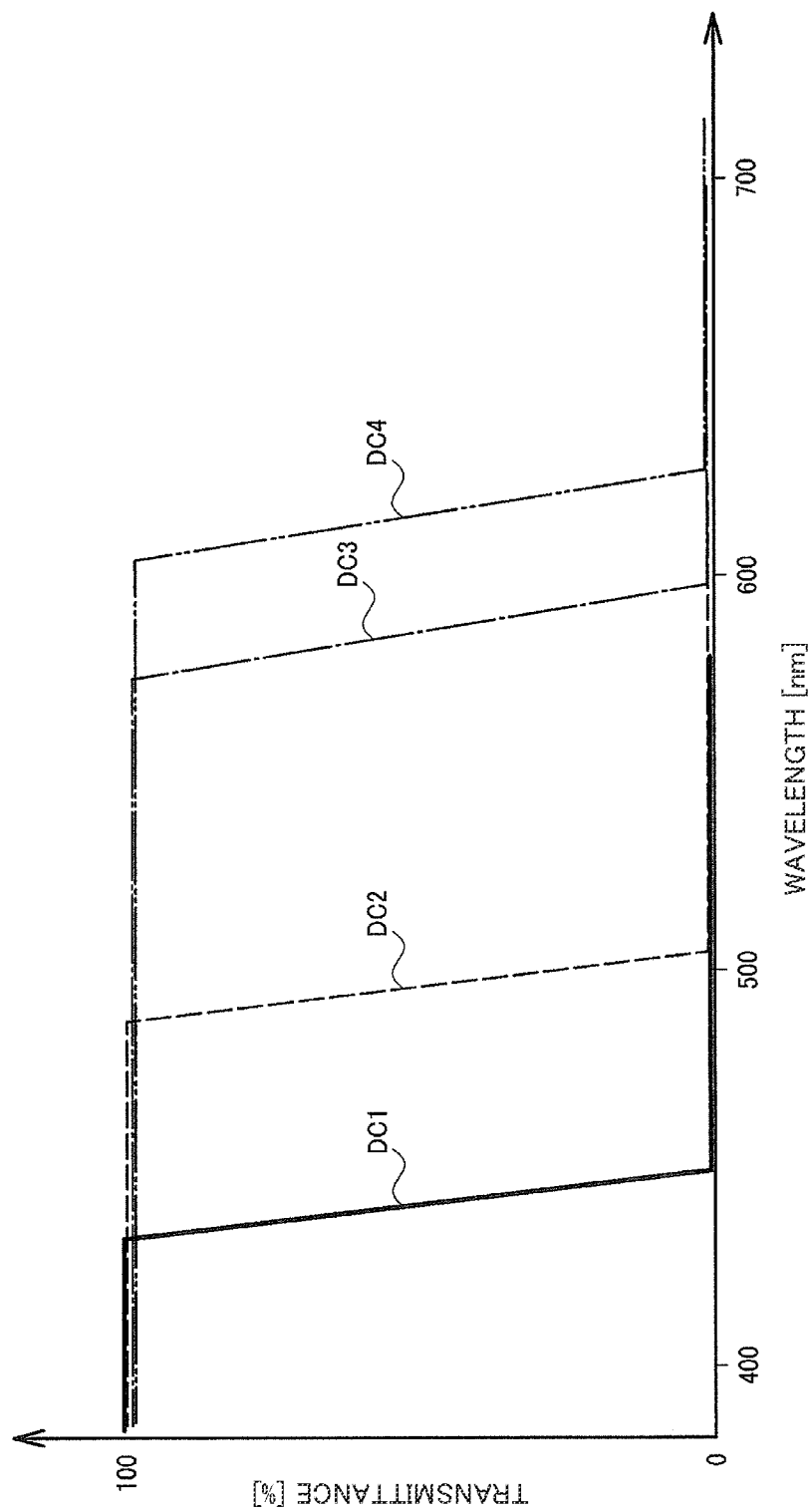

ENDOSCOPE LIGHT SOURCE DEVICE, ENDOSCOPE APPARATUS, OPERATING METHOD OF ENDOSCOPE LIGHT SOURCE DEVICE, AND LIGHT AMOUNT ADJUSTING METHOD

CROSS REFERENCE TO RELATED APPLICATION

This application is a continuation of International Patent Application No. PCT/JP2018/041802, having an international filing date of Nov. 12, 2018, which designated the United States, the entirety of which is incorporated herein by reference.

BACKGROUND

There are known illumination techniques using a combination of a plurality of semiconductor light sources each of which emits light of a different wavelength in an endoscope apparatus. A spectrum of illumination light using such illumination techniques is usually different from a spectrum of a white light source such as a xenon light source. The spectrum of the combination of the plurality of light sources is determined by a light amount ratio of the light emitted by the plurality of light sources.

Techniques for adjusting the light amount ratio of the light emitted by the plurality of light sources are disclosed by WO 2016/120907 and Japanese Unexamined Patent Application Publication No. 2016-144624, for example. According to WO 2016/120907, a plurality of lasers are used as the semiconductor light sources. The light amount ratio of the plurality of lasers is adjusted to correct individual differences of the plurality of lasers without changing color balance of the illumination light. According to Japanese Unexamined Patent Application Publication No. 2016-144624, a plurality of LEDs are used as the semiconductor light sources. An integrated value of a light amount of each of the plurality of LEDs is made to match an integrated value of a light amount of the xenon light source in a red region, green region, and blue region, so as to generate white light equivalent to that of the xenon light source.

SUMMARY

In accordance with one of some aspect, there is provided an endoscope light source device comprising:
  a light source device including four or more light sources configured to emit four or more types of light having wavelengths different from one another, and generating illumination light to illuminate an object; and
  a light source controller configured to adjust light amounts of the respective four or more types of light based on a light amount ratio setting value to be used for setting a first light amount ratio relating to color balance and a second light amount ratio relating to color representation,
  the light source device including first to fourth light sources configured to emit first to fourth light included in the four or more types of light,
  the first light and the second light being narrow band light in a blue region,
  the third light being in a green region,
  the fourth light being in a red region,
  the first light amount ratio being a ratio of a sum of the light amounts of the first light and the second light, the light amount of the third light, and the light amount of the fourth light,
  the second light amount ratio being a light amount ratio of the first light and the second light,
  the light source controller
  adjusting the light amount ratio of the first light and the second light to achieve the second light amount ratio so as to adjust the color representation from a yellow region to a red region in an image of the object.

In accordance with one of some aspect, there is an endoscope light source device comprising:
  a light source device including first to fifth light sources configured to emit first to fifth light having wavelengths different from one another, and generating illumination light to be emitted to an object; and
  a light source controller configured to adjust light amounts of the respective first to fifth light based on a light amount ratio setting value to be used for setting a first light amount ratio relating to color balance, and a second light amount ratio and a third light amount ratio relating to color representation,
  the first light and the second light being narrow band light in a blue region,
  the third light being in a green region,
  the fourth light and the fifth light being narrow band light in a red region,
  the first light amount ratio being a ratio of a sum of the light amounts of the first light and the second light, the light amount of the third light, and a sum of the light amounts of the fourth light and the fifth light,
  the second light amount ratio being a light amount ratio of the first light and the second light,
  the third light amount ratio being a light amount ratio of the fourth light and the fifth light,
  the light source controller
  adjusting the light amount ratio of the first light and the second light to achieve the second light amount ratio based on the light amount ratio setting value so as to adjust the color representation from a yellow region to a red region in an image of the object, and
  adjusting the light amount ratio of the fourth light and the fifth light to achieve the third light amount ratio based on the light amount ratio setting value so as to adjust the color representation in the red region in the image.

In accordance with one of some aspect, there is an endoscope apparatus comprising:
  the endoscope light source device as defined in claim 1; and an endoscope scope.

In accordance with one of some aspect, there is an operating method of an endoscope light source device, wherein four or more types of light belong, at least one by one, to a blue region, green region, and red region included in a wavelength region of visible light, two or more of the four or more types of light belong to a first color region that is one of the blue region, green region, and red region, the two or more types of light in the first color region are narrow band light, a first light amount ratio is a light amount ratio of the light in the blue region, the light in the green region, and the light in the red region, and a second light amount ratio is a light amount ratio of the two or more types of light in the first color region, the method comprising:
  inputting the four or more types of light having wavelengths different from one another into an endoscope scope as illumination light; and
  adjusting light amounts of the respective four or more types of light based on a light amount ratio setting value to be used for setting the first light amount ratio relating to color balance and the second light amount ratio relating to color representation, so as to adjust the color balance of the illumination light and the color representation of an image, the color representation including at least one of brightness, saturation, and hue of the image captured by an image sensor of the endoscope scope.

In accordance with one of some aspect, there is a light amount adjusting method for adjusting light amounts of a first light source and a second light source configured to emit first light and second light of narrow band light in a blue region, a third light source configured to emit third light of the narrow band light in a green region, a fourth light source and a fifth light source configured to emit fourth light and fifth light of the narrow band light in a red region, the method being performed by a light source controller and comprising:

adjusting a ratio of a sum of the light amounts of the first light and the second light, the light amount of the third light, and a sum of the light amounts of the fourth light and the fifth light to achieve a first light amount ratio based on a light amount ratio setting value so as to adjust color balance;

adjusting a light amount ratio of the first light and the second light to achieve a second light amount ratio based on the light amount ratio setting value so as to adjust color representation from a yellow region to a red region in an image of an object; and adjusting a light amount ratio of the fourth light and the fifth light to achieve a third light amount ratio based on the light amount ratio setting value so as to adjust the color representation in the red region in the image.

BRIEF DESCRIPTION OF THE DRAWINGS

FIG. 15 illustrates spectral transmittance characteristics of dichroic mirrors.

DESCRIPTION OF EXEMPLARY EMBODIMENTS

Figure 1:
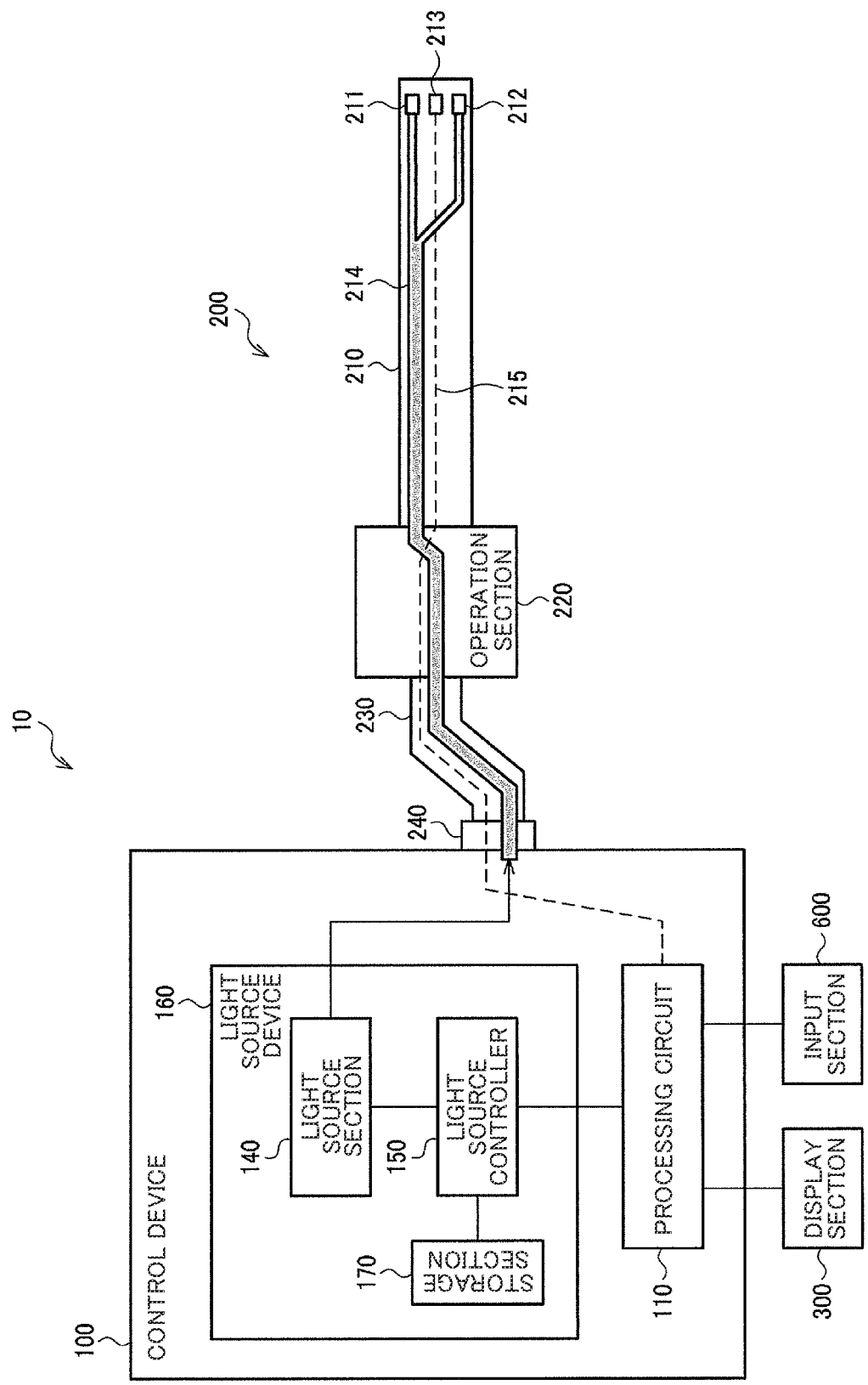
FIG. 1 illustrates a configuration example of an endoscope apparatus.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

1. Endoscope Apparatus

FIG. 1 illustrates a configuration example of an endoscope apparatus 10. Descriptions below omit configurations and operations that are common to general endoscopes and focus on descriptions about features of the present disclosure. An endoscope apparatus for medical use, such as for digestive organs, is exemplified in the description below, however, an applicable target of the present disclosure is not limited to this. That is, the endoscope apparatus used in this specification means general equipment including an insertion section for observing insides of recessed portions of various observation targets. For example, the endoscope apparatus is an endoscope apparatus for medical use that is used for a medical examination of a living body, or an endoscope apparatus for industrial use.

The endoscope apparatus 10 in FIG. 1 includes a control device 100, an endoscope scope 200, a display section 300, and an input section 600. The display section 300 is also referred to as a display, or a display device. The input section 600 is also referred to as an input device, or an operation device.

First of all, a configuration of the endoscope apparatus 10 is described.

The endoscope scope 200 includes an insertion section 210, an operation section 220, a connecting cable 230, and a connector 240. The insertion section 210 has flexibility and can be inserted into a body cavity of a living body. The body cavity of the living body is an object in the present embodiment. A user such as a physician or a surgeon holds and uses the operation section 220 to operate the endoscope apparatus 10. The connecting cable 230 connects the control device 100 and the endoscope scope 200, and has flexibility. The connector 240 is disposed at an end of the connecting cable 230 to make the endoscope scope 200 attachable to/detachable from the control device 100.

The insertion section 210 includes illumination lenses 211 and 212 and an imaging unit 213 at its distal end. The illumination lenses 211 and 212 emit illumination light toward the object, and the imaging unit 213 captures an image by receiving the illumination light reflected or scattered from a surface of the object.

The endoscope scope 200 includes a light guide path 214. The light guide path 214 is optically connected to the illumination lenses 211 and 212. The control device 100 includes a light source section 140. The light guide path 214 guides the illumination light emitted from the light source section 140 to the illumination lenses 211 and 212. The light guide path 214 is a light guide such as an optical fiber bundle. The light guide extends from the connector 240 to the illumination lenses 211 and 212 via insides of the connecting cable 230 and the operation section 220.

The illumination lenses 211 and 212 spread the illumination light guided by the light guide at a desired radiation angle. Each of the illumination lenses 211 and 212 is an illumination optical system including a single lens or a plurality of lenses.

The imaging unit 213 includes an imaging optical system and an image sensor. The image sensor is a CMOS imager, for example. The imager is a Bayer-type imager including an RGB primary color filter having a Bayer array, a complementary color imager including a complementary color filter, or a monochrome imager. The monochrome imager is used for the endoscope scope adopting a frame sequential method. The image sensor may be a CCD instead of the CMOS imager.

The endoscope scope 200 includes an image signal line 215 that transmits an image signal of an image captured by the imaging unit 213 to the control device 100. The image signal line 215 is disposed in the insertion section 210, the operation section 220, and the connecting cable 230, and is electrically connected to the control device 100 via the connector 240. The image signal line 215 may be an optical fiber for optical communication, for example.

The control device 100 includes a light source device 160 that emits the illumination light, and a processing circuit 110. The processing circuit 110 performs image processing to the image signal from the imaging unit 213 and controls each section of the endoscope apparatus 10.

The processing circuit 110 is implemented by a circuit device including a plurality of circuit components mounted on a substrate. Alternatively, the processing circuit 110 may be a processor or an integrated circuit device such as an ASIC (Application Specific Integrated Circuit). When the processing circuit 110 is the processor, the processor executes a program describing the operation of the processing circuit 110 to implement the operation of the processing circuit 110. The program is stored in a memory, not illustrated, for example.

The display section 300 displays an object image applied with the image processing by the processing circuit 110. The display section 300 is one of various common display devices, and is a liquid crystal monitor, for example. The display section 300 is electrically connected to the control device 100 by an electrical line that transmits the image signal.

The input section 600 receives the operation by the user, and outputs information on the operation to the processing circuit 110. The input section 600 is a button, a dial, a keyboard, a mouse, or a touch panel, for example. The touch panel is disposed to the display section 300. Alternatively, the input section 600 may be an interface to be connected to an information processing device such as a PC (Personal Computer). The interface receives input information from the information processing device, and outputs the input information to the processing circuit 110. The interface is a communication interface such as a USB (universal Serial Bus), or a LAN (Local Area Network), for example.

The light source device 160 includes a light source section 140 that emits the illumination light, a light source controller 150 that controls the light source section 140, and a storage section 170 that stores a light amount ratio setting value.

The light source section 140 includes four or more light sources that emit four or more types of light having wavelengths different from one another. The light source section 140 inputs the four or more types of light into the endoscope scope 200 as the illumination light. Each of the four or more light sources is a light emitting element. The light emitting element is a semiconductor light source such as an LED (Light Emitting Diode) or a semiconductor laser, for example.

A wavelength region of visible light includes a red region, a green region, and a blue region. Each region includes one of the four or more types of light included in the illumination light. In addition, any of the red region, green region, and blue region includes two or more of the four or more types of light. This region is referred to as a first color region. The two or more types of light in the first color region are narrow band light. The light other than the light in the first color region may or may not be the narrow band light. Examples of the illumination light will be described later in detail.

The light source controller 150 may include a driving circuit that drives the light sources, and a control circuit or a processor that controls the driving circuit, for example. Alternatively, when the light source includes the driving circuit, the light source controller 150 may be a control circuit or a processor that controls the driving circuit of the light source.

The light source controller 150 adjusts light amounts of the respective four or more types of light based on the light amount ratio setting value. The light amount ratio setting value is a setting value to be used for setting a first light amount ratio relating to color balance and a second light amount ratio relating to color representation. The first light amount ratio is a light amount ratio of the light in the red region, the light in the green region, and the light in the blue region. As described above, the first color region includes two or more types of light. In this case, a sum of the light amounts of the two or more types of light is the light amount of the light in the first color region. The second light amount ratio is a light amount ratio of the two or more types of light in the first color region. The light source controller 150 adjusts the light amount ratio of the four or more types of light based on the light amount ratio setting value to adjust the color balance of the illumination light and the color representation of the image. The color balance is a balance of red, green, and blue in the illumination light, and is color temperature of the illumination light, for example. The color representation of the image is different from the color balance, and is a color degree of each color such as blue or red. Specifically, the color representation includes at least one of brightness, saturation, and hue of the image. That is, adjustment of the color degree means adjustment of at least one of the brightness, saturation, and hue.

The light amount ratio setting value may be a single light amount ratio simultaneously implementing the first light amount ratio and the second light amount ratio, or may include the first light amount ratio and the second light amount ratio separately specified. An electric current value and a light emission amount have a correlation in the semiconductor light source, for example. In this case, the light amount ratio setting value may specify the electric current value to implement the first light amount ratio and the second light amount ratio. The light amount ratio setting value is stored in the storage section 170, for example. The light source controller 150 controls the illumination light based on the light amount ratio setting value read out from the storage section 170. Alternatively, the light amount ratio setting value is input to the processing circuit 110 via the input section 600. The light source controller 150 controls the illumination light based on the light amount ratio setting value received from the processing circuit 110.

The storage section 170 may be any one of various presumable storage devices. For example, the storage section 170 is a semiconductor memory such as a RAM, ROM, or a nonvolatile memory. Alternatively, the storage section 170 may be a magnetic storage device such as a hard disk drive.

The light source controller 150 may adopt any one of various presumable methods to control a light emission amount of the light source. For example, when the light source is the light emitting diode, a method such as a current light adjustment, a PWM light adjustment, a pulse number light adjustment, or a combination thereof may be adopted. In the current light adjustment, the light source controller 150 changes a driving current for driving the light emitting diode to adjust the light amount. In the PWM light adjustment, the light source controller 150 changes a light emitting time in a predetermined imaging period to adjust the light amount. In the pulse number light adjustment, the light source controller 150 changes a number of times of pulse light emission in the predetermined imaging period to adjust the light amount. The light source controller 150 may combine two or three of these three light adjustment methods.

When the plurality of light sources are used to generate the illumination light as described above, a user may desire to separately tune the color balance of the illumination light and the color representation of the image. For example, the user of the endoscope apparatus makes a diagnosis based on a color or the like of an object in an endoscopic image. In order to make the diagnosis, the user uses literatures or past experiences as reference. At this time, it is preferable that the color balance and the hue be reproduced correspondingly to the literatures or the past experiences.

According to the present embodiment, the light source controller 150 adjusts the light amount ratio of the four or more types of light included in the illumination light based on the light amount ratio setting value to adjust the color balance of the illumination light and the color representation of the image. Accordingly, the color balance of the illumination light and the color representation of the image can be separately adjusted. For example, adjustment of the light amount ratio of the four or more types of light included in the illumination light allows reproduction of the color balance and the color representation corresponding to the literatures or the past experiences.

Specifically, the light source controller 150 maintains a sum of the light amounts of the two or more types of light in the first color region within a predetermined range based on the first light amount ratio. The light source controller 150 also adjusts the light amounts of the two or more types of narrow band light in the first color region based on the second light amount ratio.

As described above, the first light amount ratio is the light amount ratio for setting the color balance of the illumination light and the second light amount ratio is the light amount ratio for setting the color representation. That is, the light source controller 150 sets the color balance of the illumination light based on the first light amount ratio, and adjusts the color representation of the image based on the second light amount ratio while maintaining the color balance. As a result, the color balance of the illumination light and the color representation of the image are separately adjusted, and target color balance and color representation can be implemented.

The predetermined range used here is an allowable range that can implement the color balance set by the first light amount ratio. For example, assume that the first light amount ratio satisfies a relation of the light amount in the red region:the light amount in the green region:the light amount in the blue region=1.1:1, and the first color region is the red region. At this time, the light amount of the red region is a sum of the light amounts of the two or more types of light in the red region. The light amount in the red region is maintained within a predetermined range from 0.9 to 1.1, for example. However, the range from 0.9 to 1.1 is an example of the predetermined range, and the predetermined range is not limited to this. The allowable range only needs to be in a range allowing correction by a general image processing technique without a large effect on an image quality. That is, when the brightness is corrected by multiplying a gain to each color band, a gain of about ±50% allows a use in a general endoscopic observation. A gain of about ±30% allows a use for various purposes without problems. A gain limited to about ±10% hardly affects image noises and hue of bright and dark portions, and allows a use in a delicate examination or treatment without problems. Moreover, with a latest image processing technique, the allowable range can be extended.

The illumination light is displayed on the display section 300 via the image sensor disposed in the endoscope scope 200. At this time, spectral characteristics of the image sensor and the display section 300 also affect the color balance. In order to set the color balance to be displayed on the display section 300 at the end to desired balance, the spectral characteristics of the image sensor and the display section 300 may be considered. More specifically, a spectral characteristic of light-receiving sensitivity of the image sensor 213, a spectral characteristic of a UV/IR cut filter disposed to the image sensor, a spectral characteristic of a color filter if the color filter is disposed, a spectral characteristic of the light guide path 214 that guides the illumination light, a spectral characteristic of the illumination lenses 211 and 212, a spectral characteristic of the imaging optical system, or the like may be considered. The first light amount ratio may be a light amount ratio set by considering one or more of these elements. Furthermore, the first light amount ratio is preferably set by considering characteristics relating to color reproduction of the display section 300.

Exemplary embodiments are described in detail below. Some of the embodiments below may be combined as appropriate.

2. First Embodiment

A first embodiment described below includes the illumination light including five types of light having wavelengths different from one another. The illumination light may include four or six or more types of light, as will be described later.

Figure 2:
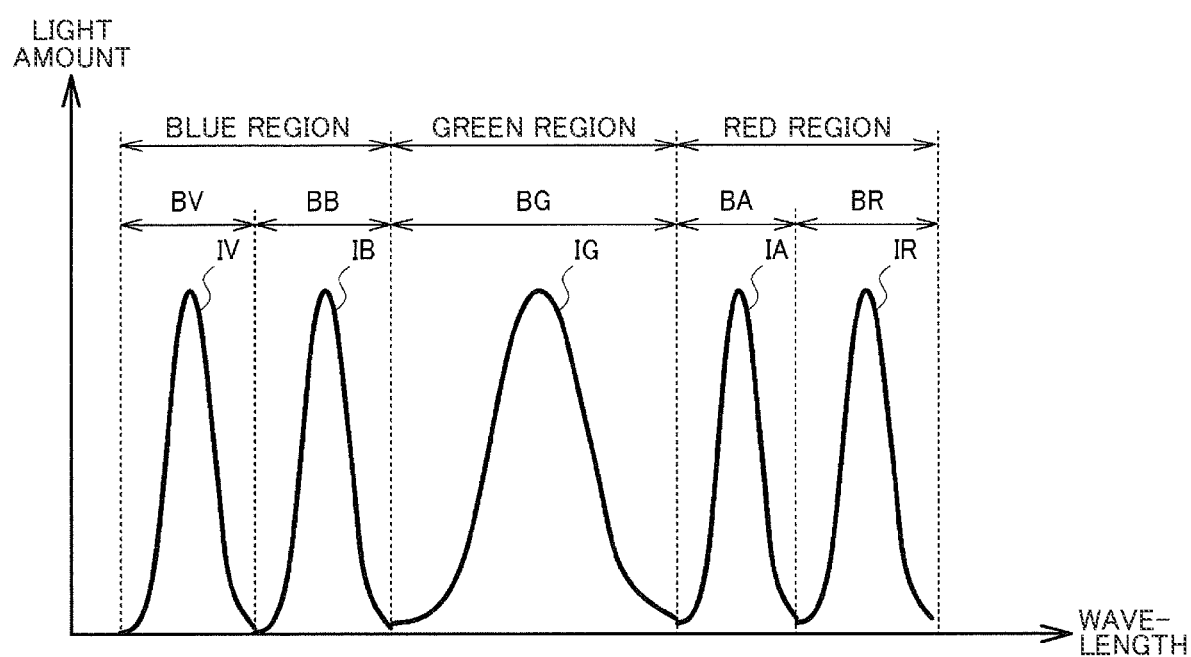
FIG. 2 is a graph illustrating an example of spectra of illumination light according to a first embodiment.

FIG. 2 illustrates an example of spectra of the illumination light according to the first embodiment. As illustrated in FIG. 2, the wavelength region of the visible light includes the blue region, green region, and red region. For example, the blue region is from 400 nm to 495 nm, the green region is from 496 nm to 585 nm, and the red region is from 585 nm to 680 nm. The wavelength region is also referred to as a wavelength band.

The blue region is divided into a region BV and a region BB, and the red region is divided into a region BA and a region BR. The illumination light includes light IV having the region BV, light IB having the region BB, light IG having a region BG, light IA having the region BA, and light IR having the region BR. The light IV, IB, IA, and IR are narrow band light. The narrow band light is light having a narrower wavelength region than a color region to which the light belongs. For example, the light IV has the region BV that is narrower than the blue region. The light IG in the green region is wide band light having the region BG of width similar to the green region. The light IG may be the narrow band light having the wavelength region narrower than the green region. The regions BV. BB, BG, BA, and BR respectively correspond to violet, blue, green, amber, and red. However, division of the region is not limited to this. The first color region described above is the blue region or the red region in FIG. 2.

Figure 3:
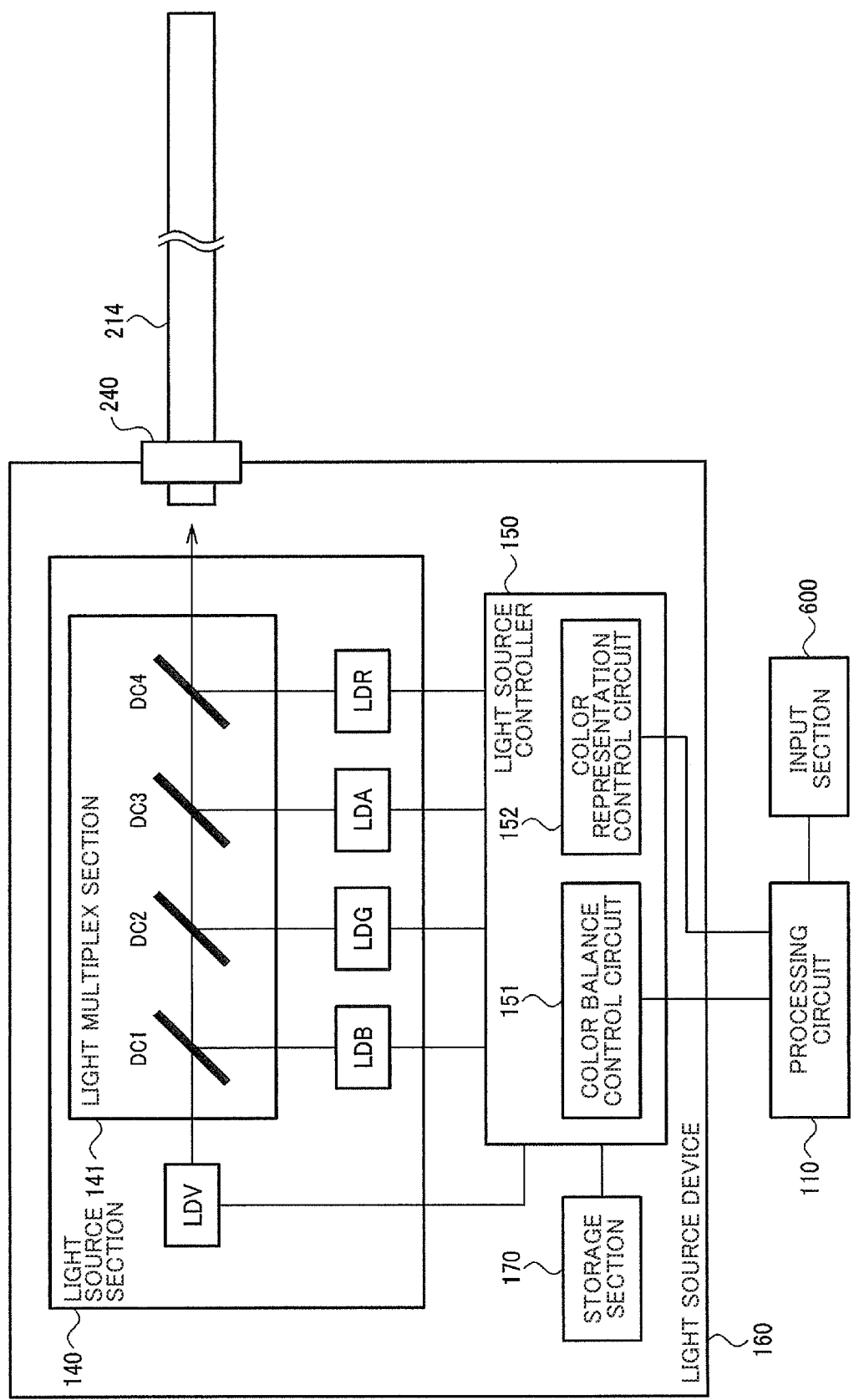
FIG. 3 illustrates a first detailed configuration example of an endoscope light source device.

FIG. 3 illustrates a first detailed configuration example of the light source device 160. FIG. 3 only illustrates the connector and the light guide path 214 of the endoscope scope 200 and omits other components.

The light source section 140 includes a light source LDV that emits the violet light IV, a light source LDB that emits the blue light IB, a light source LDG that emits the green light IG, a light source LDA that emits the amber light IA, a light source LDR that emits the red light IR, and a light multiplex section 141. The light source section 140 may further include a lens that changes light distribution of the light sources or collimates the light, or the like.

For example, the region BV of the violet light IV is 400 nm≤BV≤440 nm, the region BB of the blue light IB is 440 nm<BB≤495 nm, the region BG of the green light IG is 495 nm<BG≤585 nm, the region BA of the amber light IA is 586 nm<BA≤615 nm, and the region BR of the red light IR is 615 nm<BR≤680 nm. A boundary on a short wavelength side is set to 400 nm and a boundary on a long wavelength side is set to 680 nm. However, a wavelength component of the illumination light may exist on a side of a wavelength shorter than 400 nm or longer than 680 nm.

The light multiplex section 141 multiplexes the light in the five colors to input a resultant into the light guide path 214. The light multiplex section 141 includes dichroic mirrors DC1 to DC4 that multiplex the light IV, B, IG, IA, and IR. Alternatively, the light multiplex section 141 may be an optical fiber or an optical fiber bundle having five input ends and one output end.

The dichroic mirrors DC1 to DC4 have optical characteristics different from one another. That is, the dichroic mirror DC1 allows the light IV to pass through and reflects the light 1B. The dichroic mirror DC2 allows the light IV and IB to pass through and reflects the light IG. The dichroic mirror DC3 allows the light IV, IB, and IG to pass through and reflects the light IA. The dichroic mirror DC4 allows the light IV, IB, IG, and IA to pass through and reflects the light IR. The wording "allowing the light to pass through" used here means allowing a major part of the light including a wavelength of a peak intensity to pass through. The term "reflect" used here means reflecting the major part. That is, a skirt part of the spectrum excluded from the major part may be cut off. In other words, the dichroic mirrors DC1 to DC4 also function as filters to cut off an unnecessary part of each light. As a result, the illumination light multiplexed by the dichroic mirrors DC1 to DC4 includes five independent spectra that do not approximately overlap one another. That is, each of the regions BV, BB, BG, BA, and BR includes a single type of light, and hardly includes the light in the adjacent region.

The light source section 140 is configured to emit white illumination light and special illumination light in accordance with an observation purpose of the endoscope apparatus. For example, insertion of a filter, not illustrated, into an optical path implements the special illumination light. The filter has a spectral characteristic corresponding to a spectrum of the special light. When the light source section 140 emits the white illumination light, all the five light sources emit light and the major parts of all the five types of light enter the light guide path 214.

The light source controller 150 outputs a driving current to the light sources LDV, LDB, LDG, LDA, and LDR to cause the light sources LDV, LDB, LDG, LDA, and LDR to emit light. The light source controller 150 performs a synchronous control of emission timing of the light sources LDV, LDB, LDG. LDA, and LDR. That is, when the endoscope scope adopts the frame sequential method, the light source controller 150 causes the light sources LDV, LDB, LDG, LDA, and LDR to sequentially emit light in accordance with a predetermined light emission sequence. When the image sensor of the endoscope scope is a primary color Bayer-type image sensor or a complementary color image sensor, the light source controller 150 causes the light sources LDV, LDB, LDG, LDA, and LDR to simultaneously emit light.

The light source controller 150 includes a color balance control circuit 151 that adjusts the color balance, and a color representation control circuit 152 that adjusts the color representation.

The color balance control circuit 151 adjusts the light amount ratio of the five types of light such that the color balance of the illumination light input to an input end of the light guide path 214 connected with the connector 240 achieves the first light amount ratio. The light amounts of the light IV, IB, IG, IA, and IR are respectively defined as Bpv, Bpb, Gp, Rpa, and Rpr. The color balance control circuit 151 adjusts the light amount ratio such that a relation of (Bpy+Bpb):Gp:(Rpa+Rpr)=1:1:1 is satisfied, for example. The ratio of 1:1:1 is only an example. That is, the first light amount ratio is adjusted so as to achieve desired color temperature or color balance. The ratio of Bpv:Bpb or Rpa:Rpr can be arbitrarily set in the adjustment of the color balance. That is, even if either of the light sources is off, the color balance may be adjusted to achieve the first light amount ratio.

The color representation control circuit 152 adjusts the color representation of the image captured by the image sensor of the endoscope scope 200. That is, the color representation control circuit 152 adjusts the color representation of the image to be displayed on the display section 300. The color representation control circuit 152 adjusts the light amount ratio of Rpa:Rpr of the two types of light in the red region to achieve a red light amount ratio, so as to implement desired color representation. The color representation control circuit 152 also adjusts the light amount ratio of Bpv:Bpb of the two types of light in the blue region to achieve a blue light amount ratio, so as to implement the desired color representation. For example, the color representation control circuit 152 controls the light amount ratios to implement the color representation approximately equivalent to the color representation of an inside of a living body when the surface of the living body is illuminated by the xenon light source widely used in conventional endoscopes. In order to adjust the color representation, a color difference ΔE can be used as an index, for example.

The light amount ratio setting value is a light amount ratio determined from the first light amount ratio, the red light amount ratio, and the blue light amount ratio. In the first embodiment, the blue light amount ratio is the second light amount ratio and the red light amount ratio is a third light amount ratio. Assume that results of the adjustment of the color balance and the color representation are expressed by following equations (1) to (3), for example.

$$Bp:Gp:Rp=0.9:1.0:0.8 \quad (1)$$

$$Bpv:Bpb=0.4:0.5 \quad (2)$$

$$Rpa:Rpr=0.5:0.3 \quad (3)$$

At this time, the light amount ratio setting value is expressed by a following equation (4).

$$Bpv:Bpb:Gp:Rpa\ Rpr=0.4:0.5:1.0:0.5:0.3 \quad (4)$$

The light source controller 150 causes the light sources LDV, LDB. LDG. LDA, and LDR to emit light based on the light amount ratio setting value, so that the light source device 160 can emit the illumination light implementing both the desired color balance and color representation. For example, the color balance of the illumination light is adjusted to match the color balance achieved when the object is illuminated by the white light source such as the xenon light source. Furthermore, for example, when an image of a red object is captured, the color representation of the image is adjusted to make the object look red in the image. Furthermore, for example, the color representation of the image is adjusted to capture an image having hue similar to that of an image of a lesion part captured by the endoscope apparatus including the white light source such as the xenon light source. Furthermore, for example, the color representation of the image is adjusted to allow an easy distinction between the lesion part and a normal part.

Figure 4:
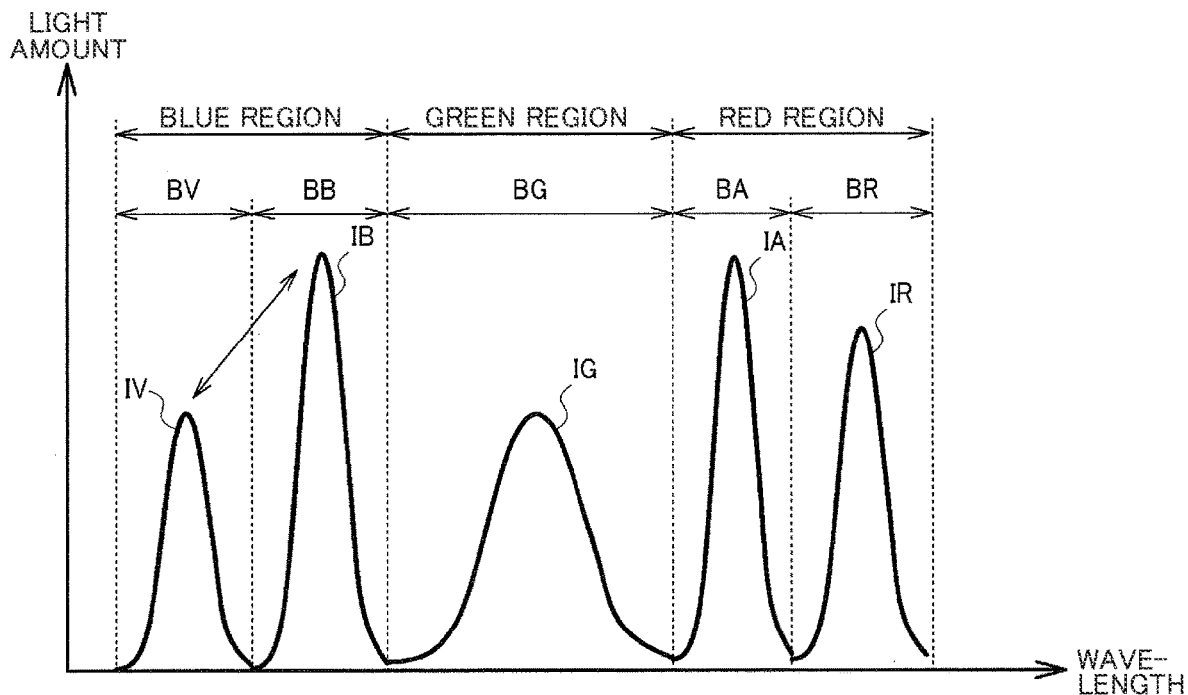
FIG. 4 is a graph illustrating a relation between a blue light amount ratio and color representation.
Figure 5:
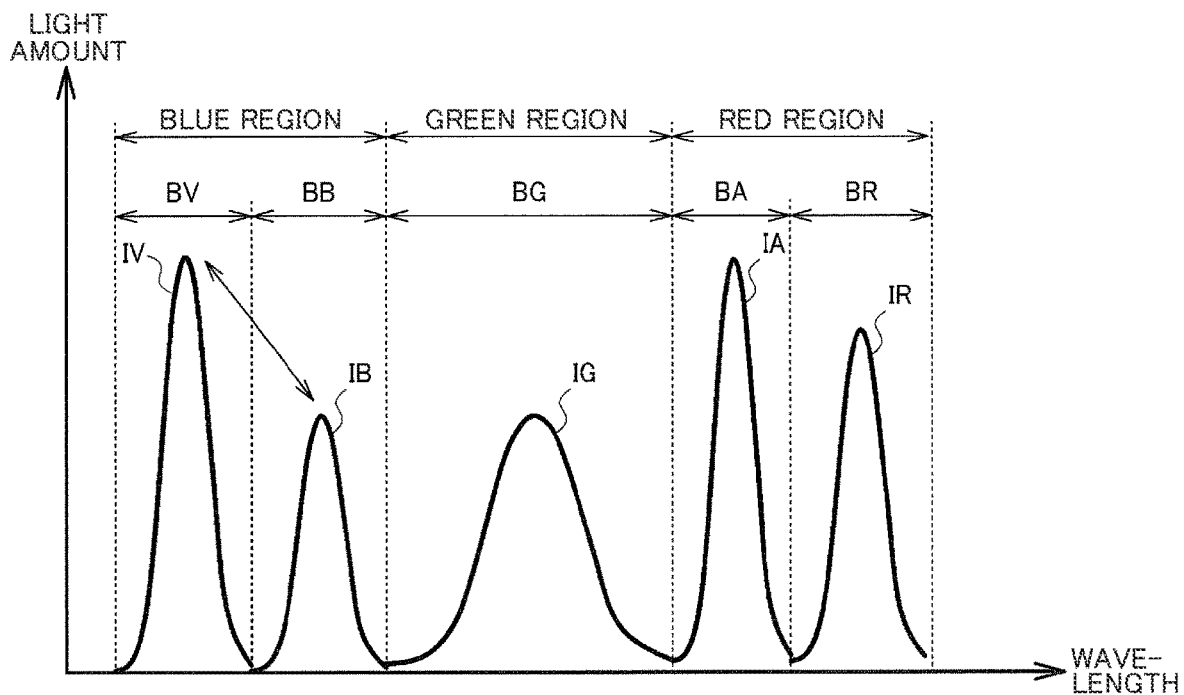
FIG. 5 is a graph illustrating the relation between the blue light amount ratio and the color representation.

FIGS. 4 and 5 are graphs illustrating relations between the blue light amount ratio of Bpv:Bpb and the color representation. By changing the light amount ratio of Bpv:Bpb of the light IV and IB in the blue region, blue and yellow in the image can be adjusted. That is, as illustrated in FIG. 4, when the light amount of the blue light IB is relatively increased, the blue in the image can be strengthened. As illustrated in FIG. 5, when the light amount of the violet light IV is relatively increased, the yellow in the image can be strengthened.

The blue region BB has higher visibility compared with visibility of the violet region BV. Accordingly, when the light amount of the violet light IV is relatively increased while the light amount of Bpv+Bpb in the blue region is maintained, the blue is relatively reduced in the image. At this time, since the color balance is maintained by the first light amount ratio of Bp:Gp:Rp, the blue is reduced while the color balance is maintained. It is considered that a reduction of the blue makes the yellow, which is a complementary color of the blue, stronger. On the other hand, when the light amount of the blue light IB is relatively increased while the light amount of Bpv+Bpb in the blue region is maintained, the blue is relatively increased in the image. Since a blue object is rare in the living body, an increase in the blue reduces the yellow, and pink is consequently strengthened. Alternatively, an addition of the blue to the red of the living body makes the living body look purplish red. This may consequently make the pink look stronger. As described above, the blue light amount ratio of Bpv:Bpb in the image in the color from the red like the living body to the color close to pale orange is controlled, so that the color representation from a yellow region to a red region can be controlled.

Figure 6:
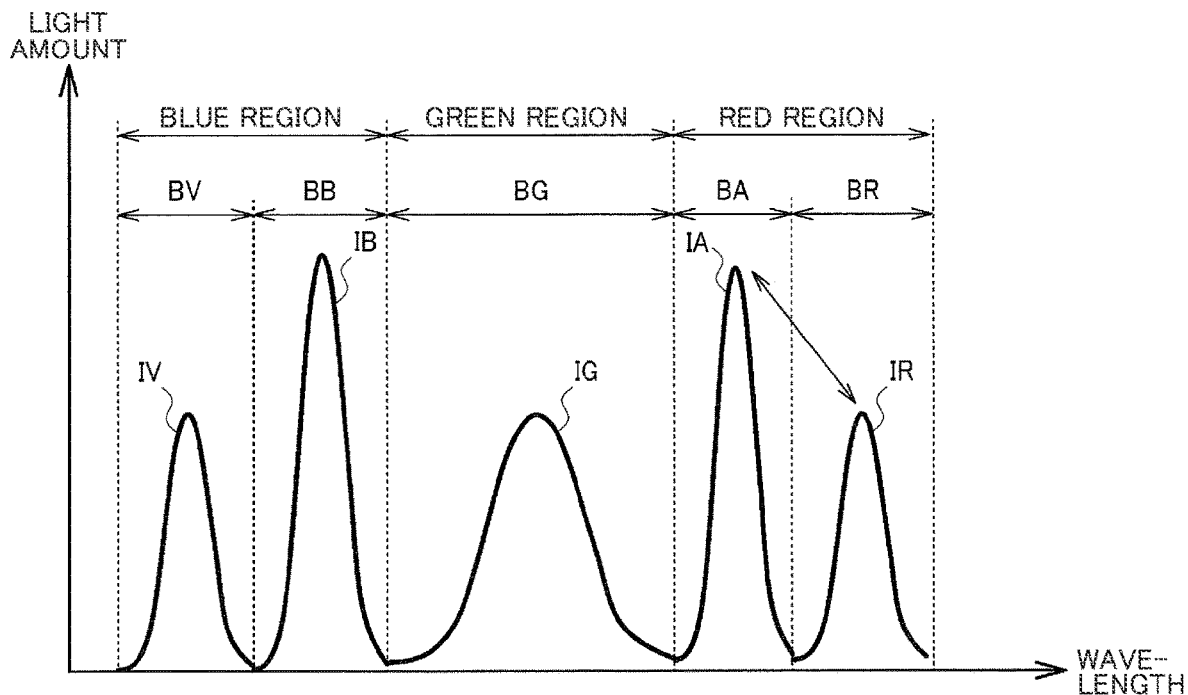
FIG. 6 is a graph illustrating a relation between a red light amount ratio and color representation.
Figure 7:
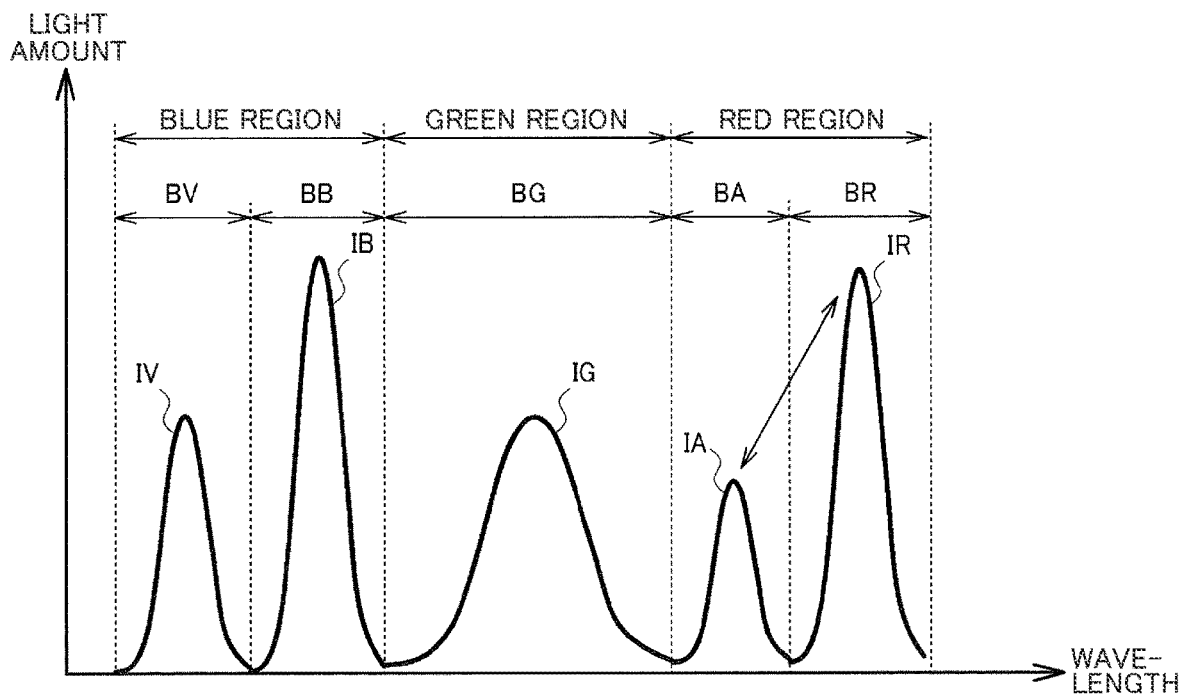
FIG. 7 is a graph illustrating the relation between the red light amount ratio and the color representation.

FIGS. 6 and 7 are graphs illustrating relations between the red light amount ratio of Rpa:Rpr and the color representation. By changing the light amount ratio of Rpa:Rpr of the light IA and IR in the red region, the red in the image can be adjusted. That is, as illustrated in FIG. 6, when the light amount of the amber light IA is relatively increased, red in the image can be weakened. As illustrated in FIG. 7, when the light amount of the red light IR is relatively increased, the red in the image can be strengthened.

The red region is a wavelength region close to the color of the living body, and thus it is considered that a correlation between the color of the light and the color of the image is high. That is, when the light amount of the amber light IA is relatively increased while the light amount of Rpa+Rpr in the red region is maintained, the red in the image is relatively reduced, and the image turns closer to orange. On the other hand, when the light amount of the red light IR is relatively increased while the light amount of Rpa+Rpr in the red region is maintained, the red in the image is relatively increased. Since the color balance is maintained by the first light amount ratio of Bp:Gp:Rp, the color representation in the red region can be adjusted while the color balance is maintained.

For example, the light amount ratio is determined by procedures described below. Firstly, an image of a sample imitating gastric mucosa is captured by the endoscope apparatus 10 according to the present embodiment. An image to be used as a target of the color representation is acquired, such as an image captured when the sample is illuminated by the xenon light source. Then, the blue light amount ratio of Bpv:Bpb and the red light amount ratio of Rpa:Rpr are set such that the color representation of an image captured by the endoscope apparatus 10 becomes similar to the color representation of the target image. This can adjust the color representation when the gastric mucosa or the like is an observation target. That is, the blue, yellow, and red in the image of the observation target can be adjusted. These light amount ratios are preferably adjusted in accordance with spectral characteristics of the image sensor and the imaging optical system included in the endoscope scope 200. These light amount ratios may also be adjusted in accordance with the observation target. These light amount ratios may also be adjusted in accordance with a preference of a user.

Next, a method for adjusting the color balance is described in detail.

In the adjustment of the color balance, the light amount ratio is set considering a characteristic of a color filter disposed to the image sensor of the endoscope scope 200 and a wavelength sensitivity characteristic of the image sensor. This adjusts the color of the illumination light when the image sensor captures the image.

Spectral shapes of the color filter of the image sensor in the blue region, green region, and red region are respectively defined as $B(\lambda)$, $G(\lambda)$, $R(\lambda)$. $\lambda$ is a wavelength. A spectral sensitivity characteristic of a pixel of the image sensor is defined as $Im(\lambda)$. The emission spectra of the light sources LDV, LDB, LDG, LDA, and LDR are respectively defined as $VL(\lambda)$, $BL(\lambda)$, $GL(\lambda)$, $AL(\lambda)$, and $RL(\lambda)$. The light amount ratio of the blue region, green region, and red region with respect to a largest light amount are respectively defined as Pb, Pg, and Pr. The largest light amount used here is the largest of the light amounts of the blue region, green region, and red region. A result of a following expression (5) integrated by a wavelength $\lambda$ is defined as Bp, a result of a following expression (6) integrated by a wavelength $\lambda$ is defined as Gp, and a result of a following expression (7) integrated by a wavelength $\lambda$ is defined as Rp.

$$B(\lambda) \times Im(\lambda) \times (VL(\lambda)+BL(\lambda)) \times Pb \quad (5)$$

$$G(\lambda) \times Im(\lambda) \times GL(\lambda) \times Pg \quad (6)$$

$$R(\lambda) \times Im(\lambda) \times (AL(\lambda)+RL(\lambda)) \times Pr \quad (7)$$

Bp represents a light amount that the image sensor receives in the blue region when an image of a white object is captured. Gp represents a light amount that the image sensor receives in the green region when the image of the white object is captured. Rp represents a light amount that the image sensor receives in the red region when the image of the white object is captured. The ratio of Bp:Gp:Rp represents the color balance. That is, the light source controller 150 adjusts the ratio of Bp:Gp:Rp such that the color of the illumination light received by the image sensor becomes a desired color, so as to adjust the color balance. At this time, even if a ratio of magnitudes of the emission spectra $VL(\lambda)$ and $BL(\lambda)$ changes, the color balance does not change as long as the integrated light amount Bp stays unchanged. In other words, even if the ratio of the magnitudes of the emission spectra $VL(\lambda)$ and $BL(\lambda)$ is adjusted within a certain range of the integrated value Bp, it does not affect the color balance.

A setting method is described above considering the spectral characteristics of the image sensor and the color filter. This method is used only when delicate color balance adjustment is necessary, and thus it is not essential. For example, when endoscope scopes of a plurality of types, each including an image sensor having a different characteristic, and the light source device 160 are combined, it is possible to acquire a single color balance as a representative value for an assumed representative image sensor, and use the representative value for other image sensors as well. This can reduce patterns of the color balance. On the contrary, the color balance may be acquired for each individual image sensor, not only for the type of image sensor. This allows acquisition and setting of delicate color balance for the individual image sensor.

Next, a method for adjusting the color representation is described in detail.

The light amount ratios of the light IV, IB, IG, IA, and IR with respect to the largest light amount are respectively defined as Pbv, Pbb, Pg, Pra, and Prr. The largest light amount is the largest of the light amounts of the light IV, IB, IG, IA, and IR. The light amount ratios Pbv, Pbb, Pra, and Prr in a first adjustment state are defined as Pbv1, Pbb1, Pra1, and Prr1. The light amount ratios Pbv, Pbb, Pra, and Prr in a second adjustment state are defined as Pbv2, Pbb2, Pra2, and Prr2.

In the adjustment of the color representation in the blue region, the light amount ratios Pbv and Pbb are adjusted within a range satisfying a following equation (8) to implement the desired color representation.

$$B(\lambda)\times Im(\lambda)\times(VL(\lambda)\times Pbv1+BL(\lambda)\times Pbb1)=B(\lambda)\times Im(\lambda)\times(VL(\lambda)\times Pbv2+BL(\lambda)\times Pbb2) \quad (8)$$

Since $B(\lambda)\times Im(\lambda)$ are identical on both sides, the light amount ratios Pbv and Pbb may be adjusted to satisfy a following equation (9) after all.

$$VL(\lambda)\times Pbv1+BL(\lambda)\times Pbb1=VL(\lambda)\times Pbv2+BL(\lambda)\times Pbb2 \quad (9)$$

In the adjustment of the color representation in the red region, the light amount ratios Pra and Prr are adjusted within a range satisfying a following equation (10) to implement the desired color representation. Similarly to the adjustment of the color representation in a blue band, it is considered that $R(\lambda)\times Im(\lambda)$ does not change.

$$AL(\lambda)\times Pba1+RL(\lambda)\times Pbr1=AL(\lambda)\times Pba2+RL(\lambda)\times Pbr2 \quad (10)$$

This way of adjustment can adjust the color representation without losing the color balance. An operator or a user may perform fine adjustment by confirming actual images when manufacturing or using the endoscope apparatus 10.

A result of a following expression (11) integrated by a wavelength $\lambda$ is defined as Bpv, a result of a following expression (12) integrated by a wavelength $\lambda$ is defined as Bpb, a result of a following expression (13) integrated by a wavelength $\lambda$ is defined as Rpa, and a result of a following expression (14) integrated by a wavelength $\lambda$ is defined as Rpr.

$$B(\lambda)\times Im(\lambda)\times VL(\lambda)\times Pbv \quad (11)$$

$$B(\lambda)\times Im(\lambda)\times BL(\lambda)\times Pbb \quad (12)$$

$$R(\lambda)\times Im(\lambda)\times AL(\lambda)\times Pba \quad (13)$$

$$R(\lambda)\times Im(\lambda)\times RL(\lambda)\times Pbr \quad (14)$$

At this time, following equations (15) and (16) hold true.

$$Bp=Bpv+Bpb \quad (15)$$

$$Rp=Rpa+Rpr \quad (16)$$

The light amount ratio setting value is Bpv:Bpb:Gp:Rpa:Rpr. This includes the first light amount ratio of Bp:Gp:Rp, the blue light amount ratio of Bpv:Bpb, and the red light amount ratio of Rpa:Rpr. As a result, parameters can be handled together as the light amount ratio. Alternatively, the first light amount ratio of Bp:Gp:Rp, the blue light amount ratio of Bpv:Bpb, and the red light amount ratio of Rpa:Rpr may be separately set as the light amount ratio setting value. As a result, parameters of the color balance and color representation are easily handled separately. For example, in order to change only the color representation while maintaining the color balance, the blue light amount ratio of Bpv:Bpb or the red light amount ratio of Rpa:Rpr may be changed.

The light amount ratio setting value may be set in accordance with the type of the endoscope scope attached to the endoscope apparatus 10. For example, the endoscope scope 200 includes a memory or the like, not illustrated, that stores an ID, and the light source controller 150 acquires the ID. The light source controller 150 identifies the image sensor based on the ID, and controls the light source section 140 based on the light amount ratio setting value corresponding to the image sensor. Alternatively, the endoscope scope 200 may include a memory or the like, not illustrated, that stores a light amount ratio setting value. The light source controller 150 may acquire the light amount ratio setting value, and control the light source section 140 based on the acquired light amount ratio setting value.

Next, operation of the light source device 160 is described. The light source device 160 includes a setting mode and a normal operation mode.

The setting mode is set when the endoscope apparatus 10 is manufactured, for example. In the setting mode, an operator operates the input section 600 to set the color balance and color representation. The processing circuit 110 outputs this setting information to the light source controller 150. The color balance control circuit 151 and the color representation control circuit 152 set the light amount ratio setting value based on the setting information, and the light source controller 150 causes the light source section 140 to emit light at the light amount ratio corresponding to the light amount ratio setting value. The operator adjusts the color balance and color representation to achieve the desired color balance and color representation. The light source controller 150 stores the light amount ratio setting value determined at the end in the storage section 170. Alternatively, the light amount ratio setting value may be automatically set in the setting mode. That is, the color representation control circuit 152 may derive the light amount ratio setting value to achieve the desired color balance and color representation based on measurement results of emission spectra of respective LEDs of the light source device, and store the light amount ratio setting value in the storage section 170.

The normal operation mode is a mode used in normal operation of the endoscope apparatus 10, i.e., a mode used when a user uses the endoscope apparatus 10. In the normal operation mode, the light source device 160 is supplied with power and activated in accordance with a normal activation sequence. When the endoscope scope 200 is connected with the light source device 160, the light source controller 150 reads out the light amount ratio setting value corresponding to the connected endoscope scope 200 from the storage section 170, and causes the light source section 140 to emit light at the light amount ratio corresponding to the light amount ratio setting value.

The light source controller 150 includes a so-called light adjustment circuit. The light adjustment circuit controls a light emission amount of the light source section 140 based on the brightness of the image so as to maintain the brightness of the image constant. The light emission amount is a total amount of the light emission amounts of the light sources LDV, LDB, LDG, LDA, and LDR. At this time, the light source controller 150 controls the light emission amount without changing the light amount ratio of Bpv:Bpb:Gp:Rpa:Rpr. That is, the brightness of the image is adjusted without changing the color balance and color representation. For example, the light source controller 150 multiplies an identical gain to the light amounts Bpv, Bpb, Gp, Rpa, and Rpr to determine the light emission amounts of the respective light sources.

According to the first embodiment described above, the light source section 140 includes first to fifth light sources (LDV, LDB, LDG, LDA, and LDR) that emit first to fifth light (IV, IB, IG, IA, and IR). The light amount ratio setting value is a setting value to be used for setting the first light amount ratio (Bp:Gp:Rp), the second light amount ratio (the blue light amount ratio of Bpv:Bpb), and the third light amount ratio (the red light amount ratio of Rpa:Rpr). The light source controller 150 adjusts the light amount ratio of the first light (IV) and the second light (IB) to achieve the second light amount ratio based on the light amount ratio setting value so as to adjust the degree of blue or yellow in the image. The light source controller 150 also adjusts the light amount ratio of the fourth light (IA) and the fifth light (IR) to achieve the third light amount ratio based on the light amount ratio setting value so as to adjust the degree of red in the image.

As a result, the color balance of the illumination light and the color representation of the image can be separately adjusted. The color balance can be adjusted to the desired color balance, and the color representation can be adjusted to the desired color representation while the color balance is maintained. Furthermore, when the light source device 160 has a light adjustment function, it is possible to provide an endoscope light source device capable of light adjustment while maintaining the adjusted color balance and color representation.

Furthermore, according to the present embodiment, the light source controller 150 adjusts the light amounts of the first to fifth light based on the light amount ratio setting value corresponding to a target of a color rendering property of the illumination light, so as to adjust the color balance of the illumination light to the color balance corresponding to the color rendering property and the color representation of the image to the color representation corresponding to the color rendering property.

As a result, the light source device 160 according to the present embodiment can generate the illumination light that reproduces the color balance and color representation of the image captured in the illumination light of the target color rendering property. The target color rendering property is a color rendering property that reproduces the color of a lesion part, for example.

Furthermore, according to the present embodiment, the light source controller 150 adjusts the light amounts of the first to fifth light based on the light amount ratio setting value that satisfies an allowable adjustment range of the first light amount ratio specified by the target color rendering property and an allowable adjustment range of the second light amount ratio specified by the target color rendering property. The light source controller 150 may also adjust the light amounts of the first to fifth light based on the light amount ratio setting value that further satisfies the allowable adjustment range of the third light amount ratio specified by the target color rendering property.

As a result, the light source device 160 according to the present embodiment can generate the illumination light that reproduces the color balance and color representation of the image captured in the illumination light of the target color rendering property within a certain allowable range.

In the first embodiment, the allowable adjustment range of the first light amount ratio includes adjustment ranges of the respective light amounts Bp, Gp, and Rp in the light amount ratio of Bp:Gp:Rp. The allowable adjustment range of the second light amount ratio includes adjustment ranges of the respective light amounts Bpv and Bpb in the light amount ratio of Bpv:Bpb. An allowable adjustment range of the third light amount ratio includes adjustment ranges of the respective light amounts Rpa and Rpr in the light amount ratio of Rpa-Rpr. These adjustment ranges are ranges in which the target color rendering property is implemented.

Furthermore, according to the present embodiment, the target color rendering property is the color balance of the xenon light source and the color representation of the image captured using the xenon light source. The color balance and color representation of the xenon light source mean the color representation of the image captured using the xenon light source. Specifically, it is preferable that the color balance and color representation be adjusted to reproduce the hue of lesion tissue represented by cancer and normal tissue. It is also preferable that the color balance and color representation be adjusted to reproduce the color balance and color representation of the xenon light source in relation to a difference in hue between a characteristic part and the normal tissue. The characteristic part is observed and diagnosed with the endoscope as to gastritis, presence and absence of *Helicobacter pylori*, or removal status of the *Helicobacter pylori*, depending on a use of the endoscope.

As a result, the light source device 160 according to the present embodiment can generate the illumination light that reproduces the color balance and color representation of the image captured using the xenon light source.

Furthermore, according to the present embodiment, the light source controller 150 adjusts the light amounts of the first to fifth light based on the light amount ratio setting value set by the spectral sensitivity characteristic of the image sensor and spectral characteristics of the first to fifth light.

As a result, the color balance and color representation of the image captured by the image sensor can be adjusted to accurate color balance and color representation considering the spectral sensitivity characteristic of the image sensor.

Furthermore, according to the present embodiment, the light source controller 150 adjusts the light amounts of the first to fifth light based on the light amount ratio setting value stored in the storage section 170.

As a result, the light source controller 150 can cause the first to fifth light sources to emit light at the first light amount ratio and the second light amount ratio designated by the light amount ratio setting value stored in the storage section 170. As a result, the illumination light can be adjusted to the desired color balance and the image can be adjusted to the desired color representation.

Furthermore, according to the present embodiment, the light source controller 150 sets the light amount ratio setting value based on the first light amount ratio set by the color balance control circuit 151 and the second light amount ratio set by the color representation control circuit 152.

As a result, the color balance control circuit 151 can adjust the color balance of the illumination light and the color representation control circuit 152 can adjust the color balance of the image.

Furthermore, according to the present embodiment, the color balance control circuit 151 sets the first light amount ratio based on the information input from the input section 600 of the endoscope apparatus 10. The color representation control circuit 152 sets the second light amount ratio based on the information input from the input section 600.

As a result, the operator or user can adjust the color balance and color representation via the input section 600.

Furthermore, according to the present embodiment, the light source controller 150 stores, in the setting mode, the light amount ratio setting value in the storage section 170 based on the first light amount ratio set by the color balance control circuit 151 and the second light amount ratio set by the color representation control circuit 152. The light source controller 150 adjusts, in the normal operation mode, the light amounts of the first to fifth light based on the light amount ratio setting value stored in the storage section 170.

As a result, in the setting mode, the light amount ratios can be set to achieve the desired color balance and color representation, and the light amount ratio setting value can be stored in the storage section 170. Then, in the normal operation mode, the illumination light achieving the desired color balance and color representation can be generated based on the light amount ratio setting value read out from the storage section 170.

3. Second Embodiment

According to a second embodiment, the user can adjust the color representation via the input section 600 in the normal operation mode. That is, the color representation control circuit 152 sets the blue light amount ratio of Bpv:Bpb and the red light amount ratio of Rpa:Rpr based on information input from the input section 600. The color balance control circuit 151 sets the first light amount ratio of Bp:Gp:Rp based on the light amount ratio setting value read out from the storage section 170.

Specifically, the user inputs the information on the desired color representation from the input section 600. The color representation control circuit 152 calculates the blue light amount ratio and the red light amount ratio to achieve the desired color representation. The light source controller 150 controls the light source section 140 based on the calculated blue light amount ratio and red light amount ratio, and the first light amount ratio.

The color representation control circuit 152 calculates the blue light amount ratio and red light amount ratio to change only the color representation without changing the color balance. For example, when the information for increasing the yellow in the image is input from the input section 600, the color representation control circuit 152 changes the ratio of Bpv:Bpb to make the color amount Bpv become relatively larger than the amount in the current ratio of Bpv:Bpb. At this time, the color representation control circuit 152 changes the ratio of Bpv:Bpb without changing a relation of Bp=Bpv+Bpb. The information on the color representation input from the input section 600 may be information on the color degree itself, or information on the change in the color degree. Alternatively, an image of the desired color representation may be read by the input section 600. Alternatively, various samples of the color representation may be stored in the input section 600 to be displayed on the display section 300 to let the user select a desired sample.

4. Third Embodiment

Figure 8:
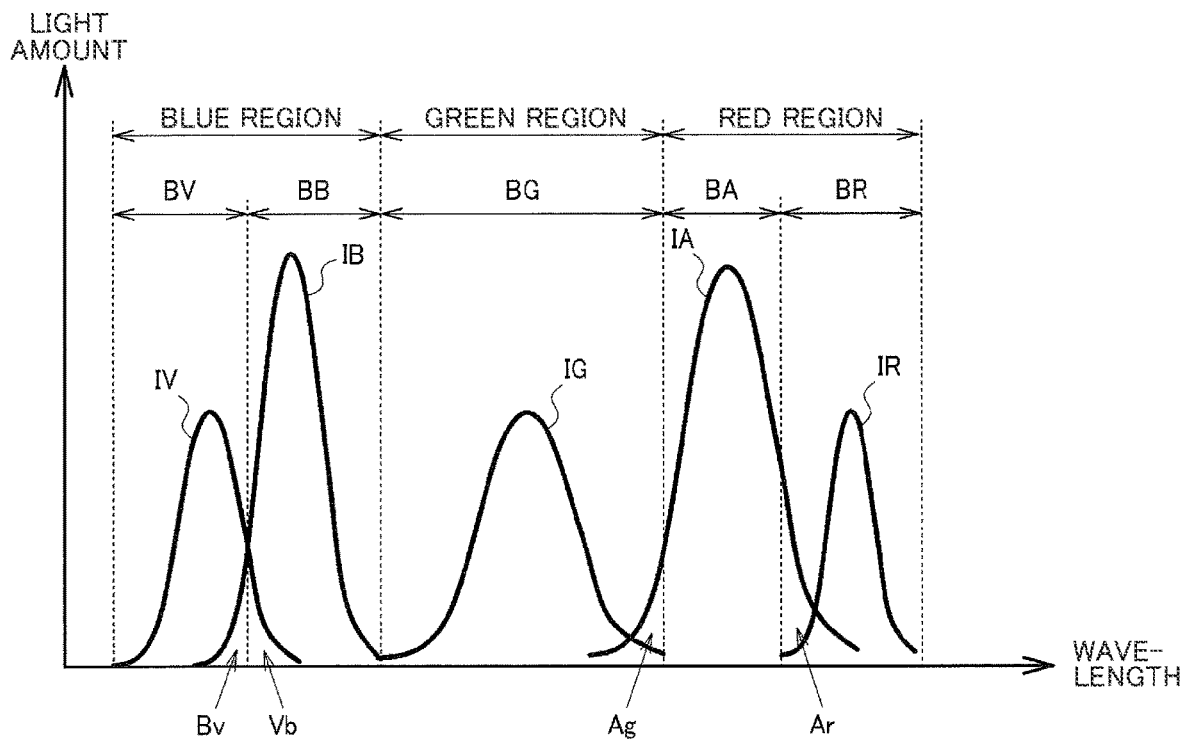
FIG. 8 is a graph illustrating an example of the spectra of the illumination light according to a third embodiment.

FIG. 8 illustrates an example of the spectra of the illumination light according to a third embodiment. As illustrated in FIG. 8, according to the third embodiment, spectra of two types of light in adjacent wavelength regions overlap each other. In FIG. 8, the spectra of the light IV and IB overlap each other, the spectra of the light IG and IA overlap each other, and the spectra of the light IA and IR overlap each other. An overlapping manner of the spectra is not limited to the one shown in FIG. 8. For example, the spectra of the light IB and IG may overlap each other.

When two adjacent spectra overlap each other, the light amount of each light needs to be calculated considering the light amount of an overlapping portion. The spectrum of the light IV has a portion $Vb(\lambda)$ protruding to the region BB, and the spectrum of the light IB has a portion $Bv(\lambda)$ protruding to the region BV. The spectrum of the light IA has a portion $Ag(\lambda)$ protruding to the region BG, and the spectrum of the light IA has a portion $Ar(\lambda)$ protruding to the region BR.

A method for calculating the color balance is described. A result of a following expression (17) integrated by a wavelength $\lambda$ is defined as Bp', a result of a following expression (18) integrated by a wavelength $\lambda$ is defined as Gp', and a result of a following expression (19) integrated by a wavelength $\lambda$ is defined as Rp' The first light amount ratio relating to the color balance is Bp':Gp':Rp'.

$$B(\lambda) \times \text{Im}(\lambda) \times (VL(\lambda) + BL(\lambda)) \times Pb \tag{17}$$

$$G(\lambda) \times \text{Im}(\lambda) \times (GL(\lambda) \times Pg + Ag(\lambda) \times Pra) \tag{18}$$

$$R(\lambda) \times \text{Im}(\lambda) \times (AL(\lambda) + RL(\lambda)) \times Pr \tag{19}$$

A method for calculating the color representation is described. A result of a following expression (20) integrated by a wavelength $\lambda$ in the region BV is defined as Bpv', a result of a following expression (21) integrated by a wavelength $\lambda$ in the region BB is defined as Bpb', a result of a following expression (22) integrated by a wavelength $\lambda$ in the region BA is defined as Rpa', and a result of a following expression (23) integrated by a wavelength $\lambda$ in the region BR is defined as Rpr'. The light amount ratio relating to the color representation includes the blue light amount ratio of Bpv':Bpb' and the red light amount ratio of Rpa':Rpr'.

$$B(\lambda) \times \text{Im}(\lambda) \times VL(\lambda) \times Pbv + BL(\lambda) \times Pbb \tag{20}$$

$$B(\lambda) \times \text{Im}(\lambda) \times BL(\lambda) \times Pbb + VL(\lambda) \times Pbv \tag{21}$$

$$R(\lambda) \times \text{Im}(\lambda) \times AL(\lambda) \times Pba \quad (22)$$

$$R(\lambda) \times \text{Im}(\lambda) \times RL(\lambda) \times Pbr + AL(\lambda) \times Pba \quad (23)$$

At this time, following equations (24) and (25) hold true.

$$Bp' = Bpv' + Bpb' \quad (24)$$

$$Rp' = Rpa' + Rpr' \quad (25)$$

As a result, the light amount ratio of the light IV, IB, IG, IA, and IR is adjusted such that the ratio of Bpv':Bpb':Gp':Rpa':Rpr' achieves the desired color balance and color representation. The adjustment method is the same as that described in the first embodiment and the like.

5. Fourth Embodiment

Figure 9:
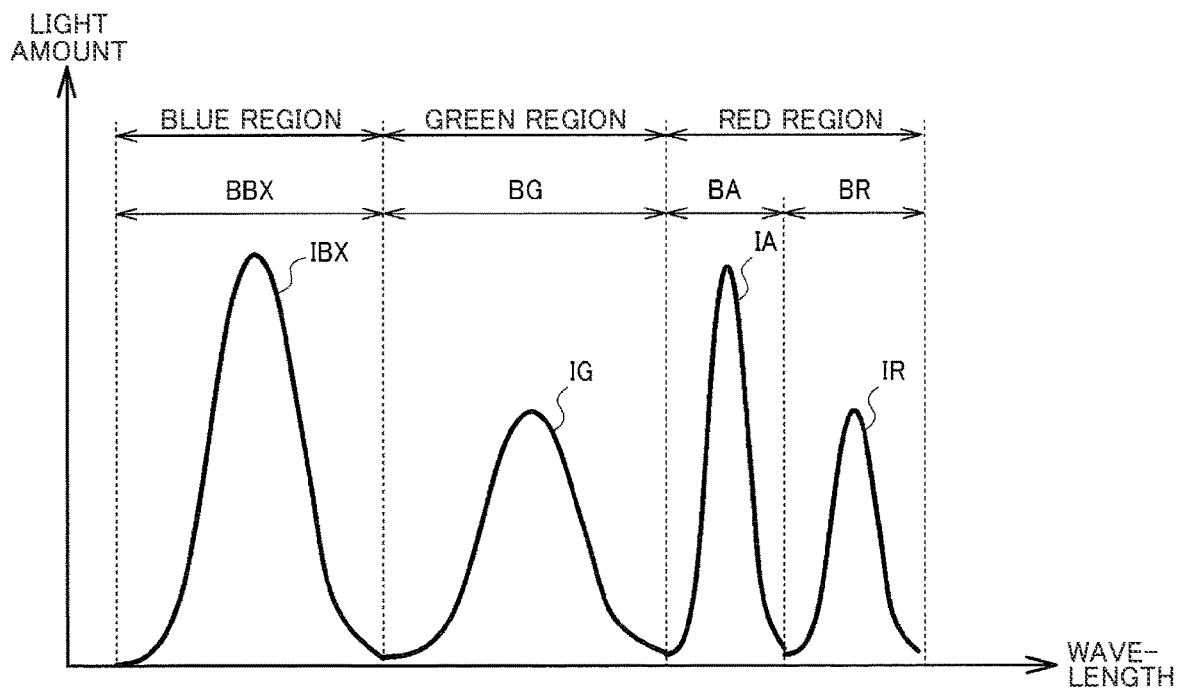
FIG. 9 is a graph illustrating an example of the spectra of the illumination light according to a fourth embodiment.

FIG. 9 illustrates an example of the spectra of the illumination light according to a fourth embodiment. According to the fourth embodiment, only the red region is divided into the region BA and the region BR, and the blue region is not divided. The illumination light includes light IBX having a region BBX, the light IG having the region BG, the light IA having the region BA, and the light IR having the region BR. The light IA and IR are the narrow band light. The light IBX in the blue region is the wide band light having the region BBX identical to the blue region. The light IBX may be the narrow band light having a wavelength region narrower than the blue region.

According to the fourth embodiment, the light source section 140 includes a first to fourth light sources that emit first to fourth light (IBX, IG, IA, and IR). The first light amount ratio is a ratio of a light amount of the first light (IBX), a light amount of the second light (IG), and a sum of light amounts of the third light (IA) and the fourth light (IR). The second light amount ratio is a ratio (the red light amount ratio of Rpa:Rpr) of the light amounts of the third light (IA) and the fourth light (IR). The light source controller 150 adjusts the light amount ratio of the third light (IA) and the fourth light (IR) to achieve the second light amount ratio based on the light amount ratio setting value so as to adjust the degree of red in the image.

As a result, the color balance of the illumination light and the red in the image can be separately adjusted. In addition, since the color representation is adjustable only in the red region, the color representation can be adjusted by the light source device 160 having a simple configuration.

6. Fifth Embodiment

Figure 10:
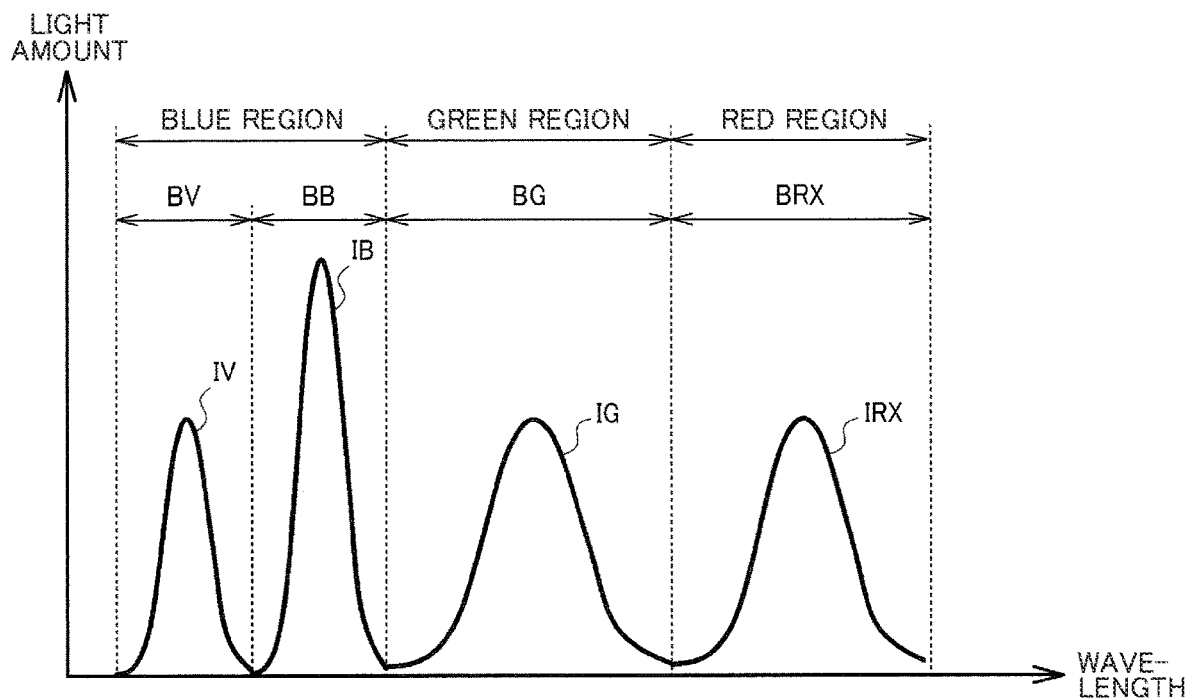
FIG. 10 is a graph illustrating an example of the spectra of the illumination light according to a fifth embodiment.

FIG. 10 illustrates an example of the spectra of the illumination light according to a fifth embodiment. According to the fifth embodiment, only the blue region is divided into the region BV and the region BB, and the red region is not divided. The illumination light includes the light IV having the region BV, the light IB having the region BB, the light IG having the region BG, and light IRX having a region BRX. The light IV and IB are the narrow band light. The light IRX in the red region is the wide band light having the region BRX identical to the red region. The light IRX may be the narrow band light having a wavelength region narrower than the red region.

According to the fifth embodiment, the light source section 140 includes first to fourth light sources that emit first to fourth light (IV, IB, IG, and IRX). The first light amount ratio is a ratio of a sum of light amounts of the first light (IV) and the second light (IB), a light amount of the third light (IG), and a light amount of the fourth light (IRX). The second light amount ratio is a ratio (the blue light amount ratio of Bpv:Bpb) of the light amounts of the first light (IV) and the second light (IB). The light source controller 150 adjusts the light amount ratio of the first light (IV) and the second light (IB) to achieve the second light amount ratio based on the light amount ratio setting value so as to adjust the degree of blue or yellow in the image.

As a result, the color balance of the illumination light and the blue or yellow in the image can be separately adjusted. In addition, since the color representation is adjustable only in the blue region, the color representation can be adjusted by the light source device 160 having a simple configuration.

7. Sixth Embodiment

Figure 11:
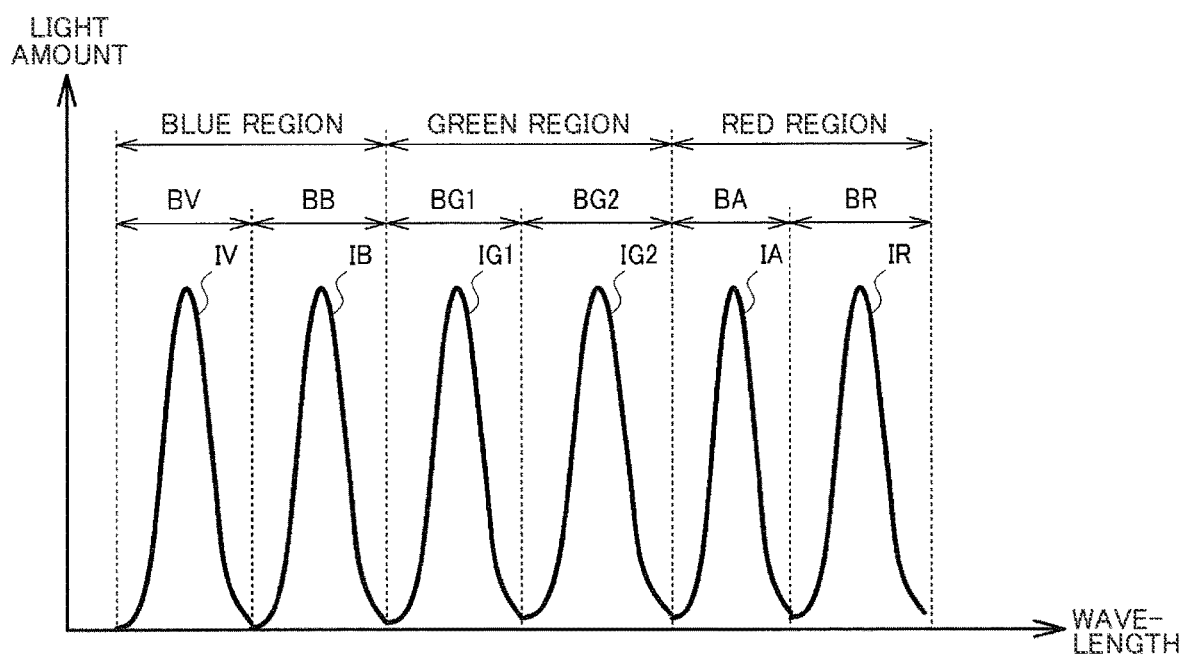
FIG. 11 is a graph illustrating an example of the spectra of the illumination light according to a sixth embodiment.

FIG. 11 illustrates an example of the spectra of the illumination light according to a sixth embodiment. According to the sixth embodiment, all the blue region, green region, and red region are divided into two regions respectively. The illumination light includes the light IV having the region BV, the light IB having the region BB, light IG1 having a region BG1, light IG2 having a region BG2, the light IA having the region BA, and the light IR having the region BR. The light IV, IB, IG1, IG2, IA, and IR are the narrow band light.

According to the sixth embodiment, the light source section 140 includes a first to sixth light sources that emit first to sixth light (IV, IB, IG1, IG2, IA and IR). The light amount ratio setting value is a setting value to be used for setting a first to fourth light amount ratios. The first light amount ratio is a ratio of a sum of light amounts of the first light (IV) and the second light (IB), a sum of light amounts of the third light (IG1) and the fourth light (IG2), and a sum of light amounts of the fifth light (IA) and the sixth light (IR). The second light amount ratio is a ratio (the blue light amount ratio of Bpv:Bpb) of the light amounts of the first light (IV) and the second light (IB). The third light amount ratio is a ratio (Gpg1:Gpg2) of the light amounts of the third light (IG1) and the fourth light (IG2). Gpg1 represents the light amount of the third light (IG1), and Gpg2 represents the light amount of the fourth light (IG2). A fourth light amount ratio is a ratio (the red light amount ratio of Rpa:Rpr) of the light amounts of the fifth light (IA) and the sixth light (IR). The light source controller 150 adjusts the light amount ratio of the first light (IV) and the second light (IB) to achieve the second light amount ratio based on the light amount ratio setting value so as to adjust the degree of blue or yellow in the image. The light source controller 150 also adjusts the light amount ratio of the third light (IG1) and the fourth light (IG2) to achieve the third light amount ratio based on the light amount ratio setting value so as to adjust the degree of green in the image. The light source controller 150 also adjusts the light amount ratio of the fifth light (IA) and the sixth light (IR) to achieve the fourth light amount ratio based on the light amount ratio setting value so as to adjust the degree of red in the image.

As a result, the color balance of the illumination light and the color representation of the image in each of the blue region, green region, and red region can be separately adjusted. Since the color representation of the image in each of the blue region, green region, and red region is adjustable, various color degrees in the image can be adjusted.

Figure 12:
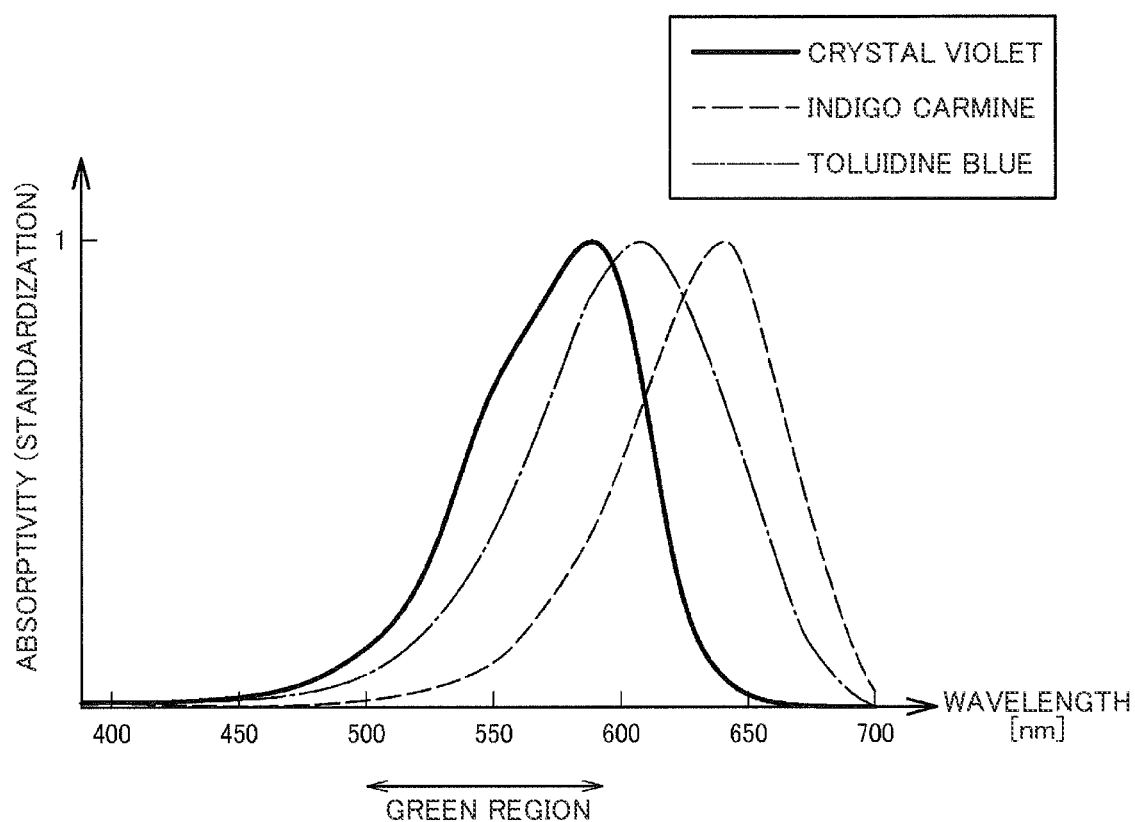
FIG. 12 is a graph illustrating spectral absorptivity characteristics of indigo carmine, crystal violet, and toluidine blue.

The adjustment of the color degree of green is described referring to FIG. 12. FIG. 12 is a graph illustrating spectral absorptivity characteristics of indigo carmine, crystal violet, and toluidine blue that are chemical agents to be sprayed and are generally used in a field of endoscopes. As illustrated in FIG. 12, these chemical agents have steep spectral absorptivity characteristics in the green region. Thus, when the light amount ratio of the light IG1 and IG2, which are in the green region and have different wavelengths, is adjusted, the color representation of the object sprayed with the chemical agents can be adjusted. For example, when the light amount of the light IG1 in green on a short wavelength side is relatively increased, the object sprayed with the chemical agents turns bluish green. When the light amount of the light IG2 in green on a long wavelength side is relatively increased, the object sprayed with the chemical agents has the color representation of yellowish green. The color representation can be adjusted such that appearance of the chemical agents becomes closer to the color representation of the xenon light source.

8. Seventh Embodiment

Figure 13:
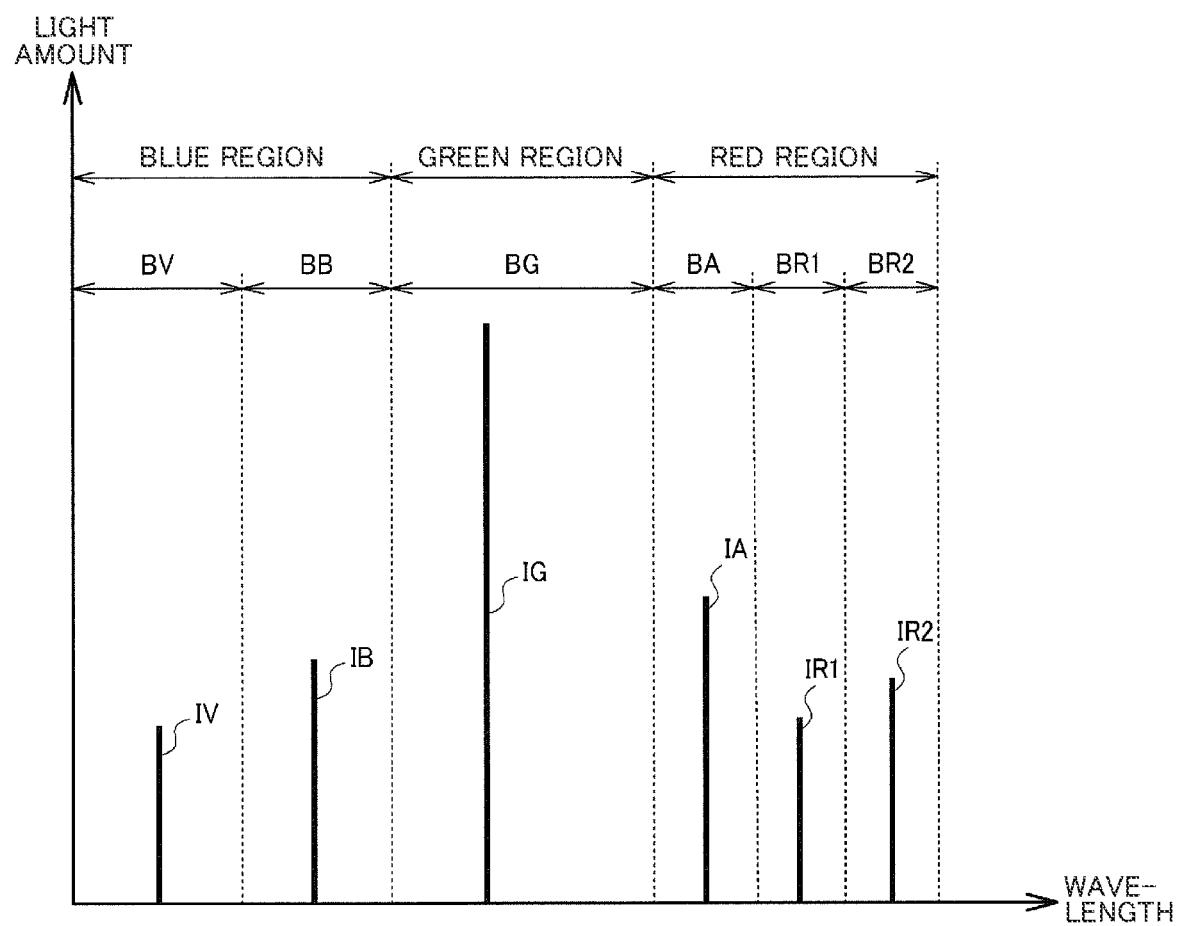
FIG. 13 is a graph illustrating an example of the spectra of the illumination light according to a seventh embodiment.

FIG. 13 illustrates an example of the spectra of the illumination light according to a seventh embodiment. According to the seventh embodiment, the red region is divided into three regions BA, BR1, and BR2. The regions BV, BB, BG, BA, BR1, and BR2 respectively include light IV, IB, IG, IA, IR1, and IR2. FIG. 13 illustrates an example of the spectra when the light sources are lasers. That is, the light IV, IB, IG, IA, IR1, and IR2 are the narrow band light of laser light.

The light source controller 150 adjusts the light amount ratio of the light IV and IB to adjust the blue or yellow in the image. The light source controller 150 also adjusts the light amount ratio in the regions BA, BR1, and BR2 to adjust the red in the image. The adjustment of the light amount ratio of the three types of light in the red region enables delicate adjustment of the color representation in the red region. Since the image of the living body includes a lot of red components, the delicate adjustment of the color representation in the red region enables more delicate adjustment of the color representation of the living body.

The seventh embodiment is described with the example using the laser as the light source, however, the light source is not limited to the laser. In addition, the first to sixth embodiments are described with the examples using the light emitting diode as the light source, however, the light source is not limited to the light emitting diode. That is, various types of light sources can be used in the first to seventh embodiments. For example, the light source may be the laser, the light emitting diode, a hybrid light source of the laser and the light emitting diode, a super luminescent diode, a light source combining the laser and a fluorescent substance, a light source combining the light emitting diode and the fluorescent substance, or a light source combining some of these.

9. Eighth Embodiment

According to an eighth embodiment, the light source controller 150 changes the light amount ratio setting value in accordance with the image sensor of the endoscope scope attached to the endoscope apparatus 10. The image sensor is a monochrome image sensor, a primary color Bayer-type image sensor, or a complementary color image sensor. The monochrome image sensor includes a UV filter, an IR filter, or the like, but does not include any color filter having different colors for pixels. The primary color Bayer-type image sensor is an image sensor including a Bayer color filter. The complementary color image sensor is an image sensor including a complementary color filter.

When the light source device 160 and the endoscope scope 200 are connected, the light source controller 150 reads out the light amount ratio setting value corresponding to the image sensor of the endoscope scope 200 connected to the light source device 160. The light amount ratio setting value corresponding to the image sensor is stored in the memory in the endoscope scope 200, or the storage section 170 in the light source device 160, for example. The light source controller 150 determines the light amount ratio of the light sources based on the read out light amount ratio setting value. As a result, the first light amount ratio and the second light amount ratio corresponding to the image sensor of the endoscope scope 200 connected to the light source device 160 are set. That is, the light amount ratios to implement the color balance and color representation corresponding to the image sensor of the endoscope scope 200 connected to the light source device 160 are set.

Furthermore, according to the eighth embodiment, the light source controller 150 may also change light emission timing of the light sources in accordance with the image sensor of the endoscope scope attached to the endoscope apparatus 10. The light emission timing of the light sources includes a frame sequential method and a simultaneous method. The frame sequential method is a method by which an image of an object illuminated by a plurality of types of light emitted in a time-division manner is captured by the monochrome image sensor. The simultaneous method is a method by which an image of an object illuminated by a plurality of types of light emitted simultaneously is captured by the image sensor.

When the light source device 160 and the endoscope scope 200 are connected, the light source controller 150 reads out information on a type of the image sensor of the endoscope scope 200 connected to the light source device 160. The information on the type of the image sensor is stored in the memory in the endoscope scope 200, or the storage section 170 in the light source device 160, for example. The light source controller 150 determines the light emission timing based on the read out information on the type of the image sensor. That is, the light source controller 150 determines whether to adopt the simultaneous light emission or the frame sequential light emission.

With the monochrome image sensor, the light source controller 150 causes the plurality of light sources to sequentially emit light based on the light amount ratio determined correspondingly to the monochrome image sensor. For example, the light source controller 150 causes the red light source LDR and the amber light source LDA to simultaneously emit light, then the green light source LDG to emit light, and then the blue light source LDB and the violet light source LDV to simultaneously emit light. With the primary color Bayer-type image sensor or the complementary color image sensor, the light source controller 150 causes the plurality of light sources to simultaneously emit light based on the light amount ratio determined correspondingly to the primary color Bayer-type image sensor or the complementary color image sensor.

According to the eighth embodiment, when a first endoscope scope is attached to the endoscope apparatus 10, the light source controller 150 adjusts the light amounts of the four or more types of light included in the illumination light based on a first light amount ratio setting value corresponding to the first endoscope scope. When a second endoscope scope is attached to the endoscope apparatus 10, the light source controller 150 adjusts the light amounts of the four or more types of light included in the illumination light based on a second light amount ratio setting value corresponding to the second endoscope scope and differing from the first light amount ratio setting value. The present embodiment is described above with the example where the light amount ratio setting value is set correspondingly to the image sensor of the endoscope scope, however, the light amount ratio setting value may be set correspondingly to the type and the like of the endoscope scope.

As a result, the color balance of the illumination light and the color representation of the image can be adjusted correspondingly to the image sensor of the endoscope scope or the type and the like of the endoscope scope attached to the endoscope apparatus 10.

10. Ninth Embodiment

Figure 14:
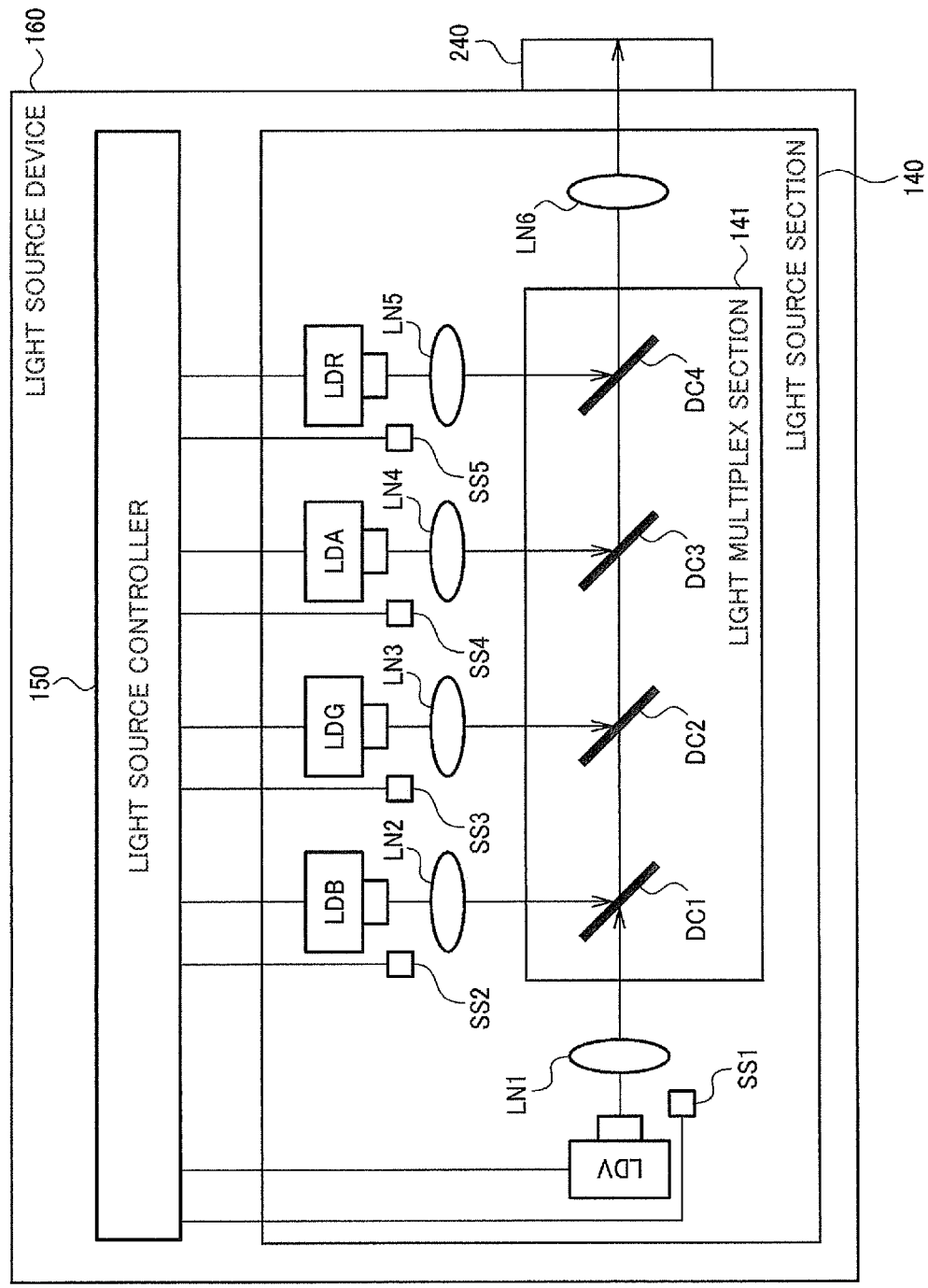
FIG. 14 illustrates a detailed configuration example of an endoscope light source device according to a ninth embodiment.

FIG. 14 illustrates a detailed configuration example of the light source device 160 according to a ninth embodiment. According to the ninth embodiment, the light source section 140 includes light sources LDV, LDB, LDG, LDA, and LDR, light sensors SS1 to SS5, lenses LN1 to LN6, and the light multiplex section 141. The light multiplex section 141 includes the dichroic mirrors DC1 to DC4.

The light sources are disposed in ascending order from the light source on a short wavelength side, from a far side toward a near side of the connector 240 connected with the endoscope scope. The lens LN1 inputs the light emitted by the light source LDV into the dichroic mirror DC1. Similarly, the lenses LN2, LN3, LN4, and LN5 respectively input the light emitted by the light sources LDB, LDG, LDA, and LDR into the dichroic mirrors DC1, DC2. DC3, and DC4. The dichroic mirrors DC1 to DC4 multiplex the light emitted by the light sources LDB, LDG, LDA, and LDR. The lens LN6 inputs the multiplexed light into the connector 240.

The light sensor SS1 is disposed outside an optical path from the light source LDV toward the lens LN1. That is, the light sensor SS1 detects leaking light that is part of the light emitted from the light source LDV and is leaking outside the optical path. Similarly, the light sensors SS2, SS3, SS4, and SS5 respectively disposed outside optical paths from the light sources LDB, LDG, LDA and LDR toward the lenses LN2, LN3, LN4, and LN5. That is, the light sensors SS2, SS3, SS4, and SS5 respectively detect leaking light that is part of the light emitted from the light sources LDB, LDG, LDA, and LDR and is leaking outside the optical paths. Light receiving planes of the light sensors SS1 to SS5 face emitting planes of the light sources. Thus, the light sensors SS1 to SS5 are not likely to receive reflected and scattered light from the lenses and the dichroic mirrors. The light sensor SS1 includes an optical filter having a wavelength characteristic equivalent to attenuation caused when the light from the light source LDV passes through the light multiplex section 141. Similarly, the light sensors SS2 to SS5 respectively include optical filters having the wavelength characteristics equivalent to the attenuation caused when the light from the light sources LDB, LDG, LDA, and LDR pass through the light multiplex section 141. The term "equivalent" includes being approximately equivalent. That is, the wavelength characteristic of the optical filter is not limited to be exactly equivalent to the attenuation caused when the light passes through the light multiplex section 141. The light sensors SS1 to SS5 may include an ND (Neutral Density) filter for optimizing a range of a light receiving amount.

FIG. 15 illustrates the spectral transmittance characteristics of the dichroic mirrors DC1 to DC4. The dichroic mirrors DC1 to DC4 are dielectric multilayer mirrors. The spectral transmittance characteristics of all the dichroic mirrors DC1 to DC4 are high in transmittance on the short wavelength side (approximately 100%) and low in transmittance on the long wavelength side (approximately 0%). A dielectric multilayer film mirror reflects almost entire light that does not pass through it. That is, an approximate reflectance is a value obtained by subtracting the transmittance from 100%. It is preferable that a change in transmittance of each dichroic mirror be designed to be as steep as possible. However, it is also preferable that it be designed to have a suitable slope considering cost or the like.

According to the spectral transmittance characteristics illustrated in FIG. 15, the transmittance characteristics of all the dichroic mirrors are high on the short wavelength side and low on the long wavelength side. Thus, even when atmosphere temperature changes, for example, wavelength shifts occur to the transmittance characteristics of all the dichroic mirrors in a same direction. As a result, a change in the light amount of the illumination light emitted from the light source device 160 can be made small. In addition, even if the atmosphere temperature changes, a change in the light amount ratio can also be made small for a similar reason.

The light source controller 150 adjusts the light emission amounts of the light sources LDV, LDB, LDG, LDA, and LDR based on the light amounts sensed by the light sensors SS1 to SS5 such that the illumination light emitted from the endoscope scope on the object achieves the light amount ratio indicated by the light amount ratio setting value.

That is, the light source controller 150 calculates the actual light amount ratio based on the light amounts sensed by the light sensors SS1 to SS5, compares the calculated light amount ratio with the light amount ratio setting value, and performs feedback control of the light emission amounts of the light sources LDV, LDB, LDG, LDA, and LDR based on a comparison result. As a result, variations in the light emission amounts due to individual differences of the light sources, or changes in the light emission amounts due to aging deterioration of the light sources can be corrected by the feedback control. This can implement the accurate light amount ratio, and thus can implement the accurate color balance and color representation.

The light sensors SS1 to SS5 include optical filters that have the wavelength characteristics equivalent to the attenuation caused when the light emitted from the light sources LDV. LDB, LDG, LDA, and LDR pass through the light multiplex section 141. As described above, the term "equivalent" includes being approximately equivalent. The light source controller 150 adjusts the light amounts of light based on output from the light sensors SS1 to SS5.

That is, the light emission amounts of the light sources multiplied by attenuation rates at the light multiplex section 141 are the light amounts at an emission end of the light multiplex section 141. With the optical filters disposed to the light sensors SS1 to SS5, the light receiving amounts of the light sensors SS1 to SS5 are set by considering the attenuation at the light multiplex section 141. The light source controller 150 adjusts the light emission amounts based on the output of the light sensors SS1 to SS5 to perform the feedback control of the light emission amounts of the light sources such that the light amounts at the emission end of the light multiplex section 141 satisfy the light amount ratio setting value. As a result, since the light amounts at the emission end of the light multiplex section 141 satisfy the light amount ratio setting value, the accurate color balance and color representation can be implemented. The light sensors SS1 to SS5 may include wavelength cut filters. The dichroic mirrors DC1 to DC 4 are disposed on the optical paths of the light emitted from the light sources LDV, LDB, LDG, LDA, and LDR toward the connector 240. The wavelength cut filters remove light in wavelength bands cut by the dichroic mirrors DC1 to DC4. As a result, more accurate feedback control of the light emission amounts of the light sources can be performed with respect to the light amount ratio setting value.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:

1. An endoscope light source device comprising:
   a light source device comprising first to fourth light sources configured to emit first to fourth lights having wavelengths different from one another as illumination light to illuminate an object; and
   a light source controller configured to adjust light amounts of the respective first to fourth lights based on a light amount ratio setting value to be used for setting a first light amount ratio relating to color balance of the illumination light and a second light amount ratio relating to color representation,
   wherein the first light and the second light are narrow band lights in a blue region,
   wherein the third light is in a green region,
   wherein the fourth light is in a red region,
   wherein the first light amount ratio is a ratio of a sum of the light amounts of the first light and the second light to the light amount of the third light to the light amount of the fourth light,
   wherein the second light amount ratio is a light amount ratio of the first light and the second light, and
   wherein the light source controller is configured to:
      adjust the color balance of the illumination light based on the first light amount ratio; and
      adjust the color representation from a yellow region to a red region in an image of the object based on the second light amount ratio while maintaining the adjusted color balance of the illumination light.

2. The endoscope light source device as defined in claim 1,
   wherein the light source controller is configured to:
      maintain the sum of the light amounts of the first light and the second light in the blue region within a predetermined range based on the first light amount ratio; and
      adjust the light amounts of the first light and the second light in the blue region based on the second light amount ratio.

3. The endoscope light source device as defined in claim 1,
   wherein the light source device comprises a fifth light source configured to emit fifth light,
   wherein the fifth light is a narrow band light in the red region,
   wherein the light amount ratio setting value is a setting value to be used for setting the first light amount ratio, the second light amount ratio, and a third light amount ratio,
   wherein the first light amount ratio is a ratio of the sum of the light amounts of the first light and the second light to the light amount of the third light to a sum of light amounts of the fourth light and the fifth light,
   wherein the second light amount ratio is the light amount ratio of the first light and the second light,
   wherein the third light amount ratio is a light amount ratio of the fourth light and the fifth light, and
   wherein the light source controller is configured to:
      adjust the color representation from the yellow region to the red region in the image of the object based on the second light amount ratio while maintaining the adjusted color balance of the illumination light, and
      adjust the color representation in the red region in the image of the object based on the third light amount ratio while maintaining the adjusted color balance of the illumination light.

4. The endoscope light source device as defined in claim 1,
   wherein the light source controller is configured to adjust the light amounts of the respective first to fourth lights based on the light amount ratio setting value corresponding to a target of a color rendering property of the illumination light so as to adjust the color balance of the illumination light to color balance corresponding to the color rendering property, and the color representation of the image to color representation corresponding to the color rendering property.

5. The endoscope light source device as defined in claim 4,
   wherein the light source controller is configured to adjust the light amounts of the respective first to fourth lights based on the light amount ratio setting value that satisfies an allowable adjustment range of the first light amount ratio specified by the target of the color rendering property and an allowable adjustment range of the second light amount ratio specified by the target of the color rendering property.

6. The endoscope light source device as defined in claim 4,
   wherein the target of the color rendering property includes color balance of a xenon light source and color representation of an image captured using the xenon light source.

7. The endoscope light source device as defined in claim 1,
   wherein the light source controller is configured to adjust the light amounts of the respective first to fourth lights based on the light amount ratio setting value set by a spectral sensitivity characteristic of an image sensor and spectral characteristics of the first to fourth lights.

8. The endoscope light source device as defined in claim 1, further comprising a storage device configured to store the light amount ratio setting value, wherein the light source controller is configured to adjust the light amounts of the respective first to fourth lights based on the light amount ratio setting value stored in the storage device.

9. The endoscope light source device as defined in claim 1,
wherein the light source controller comprises:
a color balance control circuit configured to set the first light amount ratio; and
a color representation control circuit configured to set the second light amount ratio, and
wherein the light source controller is configured to set the light amount ratio setting value based on the first light amount ratio set by the color balance control circuit and the second light amount ratio set by the color representation control circuit.

10. The endoscope light source device as defined in claim 9,
wherein the color balance control circuit is configured to set the first light amount ratio based on information input from an input section of an endoscope apparatus, and
wherein the color representation control circuit is configured to set the second light amount ratio based on the information input from the input section.

11. The endoscope light source device as defined in claim 10, further comprising a storage device,
wherein the light source controller is configured to:
store, in a setting mode, the light amount ratio setting value in the storage device based on the first light amount ratio set by the color balance control circuit and the second light amount ratio set by the color representation control circuit; and
adjust, in a normal operation mode, the light amounts of the first to fourth lights based on the light amount ratio setting value stored in the storage device.

12. The endoscope light source device as defined in claim 1,
wherein the light source controller is configured to:
adjust the light amounts of the respective first to fourth lights based on a first light amount ratio setting value corresponding to a first endoscope scope; and
adjust the light amounts of the respective first to fourth lights based on a second light amount ratio setting value corresponding to a second endoscope scope and differing from the first light amount ratio setting value.

13. The endoscope light source device as defined in claim 12,
wherein the first endoscope scope and the second endoscope scope are any two of an endoscope scope adopting a frame sequential method in which the image of the object illuminated by the first to fourth lights in a time-division manner is captured by a monochrome image sensor, an endoscope scope of a primary color type in which the image of the object illuminated by the illumination light is captured by a primary color Bayer-type image sensor, and an endoscope scope of a complementary color type in which the image of the object illuminated by the illumination light is captured by a complementary color image sensor.

14. The endoscope light source device as defined in claim 1, further comprising light sensors configured to sense the light amounts of the respective first to four lights,
wherein the light source controller is configured to adjust the light amounts of the first to fourth lights based on the light amounts sensed by the light sensors such that the illumination light emitted to the object achieves the light amount ratio indicated by the light amount ratio setting value.

15. The endoscope light source device as defined in claim 14,
wherein the light source device comprises:
a light multiplex device configured to input the first to fourth lights into an endoscope scope,
wherein the light sensors comprises optical filters having wavelength characteristics equivalent to attenuation caused when the first to fourth lights pass through the light multiplex device, and
wherein the light source controller is configured to adjust the light amounts of the first to fourth lights based on output from the light sensors.

16. An endoscope light source device comprising:
a light source device comprising first to fourth light sources configured to emit first to fifth lights having wavelengths different from one another as illumination light to illuminate an object; and
a light source controller configured to adjust light amounts of the respective first to fifth lights based on a light amount ratio setting value to be used for setting a first light amount ratio relating to color balance of the illumination light, and a second light amount ratio and a third light amount ratio relating to color representation,
wherein the first light and the second light a narrow band lights in a blue region,
wherein the third light is in a green region,
wherein the fourth light and the fifth light a narrow band lights in a red region,
wherein the first light amount ratio is a ratio of a sum of the light amounts of the first light and the second light to the light amount of the third light to a sum of the light amounts of the fourth light and the fifth light,
wherein the second light amount ratio is a light amount ratio of the first light and the second light,
wherein the third light amount ratio is a light amount ratio of the fourth light and the fifth light, and
wherein the light source controller is configured to:
adjust the color balance of the illumination light based on the first light amount ratio;
adjust the color representation from a yellow region to a red region in an image of the object based on the second light amount ratio while maintaining the adjust color balance; and
adjust the color representation in the red region in the image based on the third light amount ratio while maintaining the adjusted color balance.

17. An endoscope apparatus comprising:
the endoscope light source device as defined in claim 1; and
an endoscope scope.

18. A method of operating an endoscope light source device,
wherein the endoscope light source device comprises:
a light source device comprising first to fourth light sources configured to emit first to fourth lights having wavelengths different from one another as illumination light to illuminate an object; and
a light source controller configured to adjust light amounts of the respective first to fourth lights based on a light amount ratio setting value to be used for setting a first light amount ratio relating to color balance of the illumination light and a second light amount ratio relating to color representation, wherein the first light and the second light are narrow band lights in a blue region, wherein the third light is in a green region, wherein the fourth light is in a red region, wherein the first light amount ratio is a ratio of a sum of the light amounts of the first light and the second light to the light amount of the third light to the light amount of the fourth light, and wherein the second light amount ratio is a light amount ratio of the first light and the second light, and wherein the method comprises:

adjusting, by the light source controller, the color balance of the illumination light based on the first light amount ratio; and adjusting, by the light source controller, the color representation from a yellow region to a red region in an image of the object based on the second light amount ratio while maintaining the adjusted color balance of the illumination light.

19. A method of operating an endoscope light source device, wherein the endoscope light source device comprises:

a light source device comprising first to fourth light sources configured to emit first to fifth lights t having wavelengths different from one another as illumination light to illuminate an object; and a light source controller configured to adjust light amounts of the respective first to fifth lights based on a light amount ratio setting value to be used for setting a first light amount ratio relating to color balance of the illumination light, and a second light amount ratio and a third light amount ratio relating to color representation, wherein the first light and the second light are narrow band lights in a blue region, wherein the third light is in a green region, wherein the fourth light and the fifth light are narrow band lights in a red region, wherein the first light amount ratio is a ratio of a sum of the light amounts of the first light and the second light to the light amount of the third light to a sum of the light amounts of the fourth light and the fifth light, wherein the second light amount ratio is a light amount ratio of the first light and the second light, and wherein the third light amount ratio is a light amount ratio of the fourth light and the fifth light, and wherein the method comprises:

adjusting, by the light source controller, the color balance of the illumination light based on the first light amount ratio;

adjusting, by the light source controller, the color representation from a yellow region to a red region in an image of the object based on the second light amount ratio while maintaining the adjust color balance; and adjusting, by the light source controller, the color representation in the red region in the image based on the third light amount ratio while maintaining the adjusted color balance.

* * * * *